United States Patent
Ries et al.

(10) Patent No.: US 6,451,832 B2
(45) Date of Patent: *Sep. 17, 2002

(54) BENZIMIDAZOLES WITH ANTITHROMBOTIC ACTIVITY

(75) Inventors: Uwe Ries, Biberach; Iris Kaufmann-Hefner, Attenweiler; Norbert Hauel, Schemmerhofen; Henning Priepke, Warthausen; Herbert Nar, Mittelbiberach; Jean Marie Stassen, Bad Buchau; Wolfgang Wienen, Biberach, all of (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/735,159

(22) Filed: Dec. 12, 2000

Related U.S. Application Data
(60) Provisional application No. 60/175,163, filed on Jan. 7, 2000.

(30) Foreign Application Priority Data

Dec. 23, 1999 (DE) .......................... 199 62 329

(51) Int. Cl.[7] ................... A61K 31/4184; C07D 403/06
(52) U.S. Cl. ................... 514/394; 514/364; 514/381; 548/131; 548/254; 548/306.1
(58) Field of Search ................... 548/131, 254, 548/306.1; 514/364, 381, 394

(56) References Cited

U.S. PATENT DOCUMENTS

| | | | |
|---|---|---|---|
| 4,634,783 A | 1/1987 | Fuji et al. | |
| 4,882,342 A | * 11/1989 | Von Der Saal et al. | 514/338 |
| 5,434,150 A | 7/1995 | Austel et al. | |
| 5,972,968 A | 10/1999 | De Nanteuil et al. | |
| 6,248,770 B1 | 6/2001 | Ries et al. | |

FOREIGN PATENT DOCUMENTS

| | | |
|---|---|---|
| DE | 198 57 202 | 3/1999 |
| DE | 199 12 690 | 4/1999 |
| DE | 198 29 964 A | 1/2000 |
| DE | 198 29 964 | 1/2000 |
| JP | 11-100368 | 4/1999 |
| WO | WO94 08962 | 4/1994 |
| WO | WO97 21437 | 6/1997 |
| WO | WO98 01428 | 1/1998 |
| WO | WO98 37075 | 8/1998 |
| WO | WO99 40072 A | 8/1999 |
| WO | WO00 01704 A | 1/2000 |

* cited by examiner

Primary Examiner—Laura L. Stockton
(74) Attorney, Agent, or Firm—Robert P. Raymond; Alan R. Stempel; Mary-Ellen M. Devlin

(57) ABSTRACT

Novel benzimidazoles having antithrombotic activity. Exemplary are:

(a) 2-(4-amidinophenylaminomethyl)-1-methyl-5-[1-(ethoxycarbonylmethylamino)-1-(2,5-dihydropyrrolocarbonyl)-ethyl]-benzimidazole, (b) 2-[4-(N-phenylcarbonylamidino)-phenylaminomethyl]-1-methyl-5-[1-(ethoxycarbonylmethylamino)-1-(2,5-dihydropyrrolocarbonyl)-ethyl]-benzimidazole, and (c) (R)-2-[4-(N-phenylcarbonylamidino)-phenylaminomethyl]-1-methyl-5-[1-(isobutyloxycarbonylmethylamino)-1-(pyrrolidinocarbonyl)-ethyl]-benzimidazole.

4 Claims, No Drawings

BENZIMIDAZOLES WITH ANTITHROMBOTIC ACTIVITY

RELATED APPLICATIONS

Benefit of U.S. Provisional Application Ser. No. 60/175,163, filed on Jan. 7, 2000, is hereby claimed.

FIELD OF THE INVENTION

The present invention relates to novel benzimidazoles, methods for making them, pharmaceutical compositions comprising them, and their use as, inter alia, antithrombotic agents.

DESCRIPTION OF THE INVENTION

The present invention relates to benzimidazoles of general formula

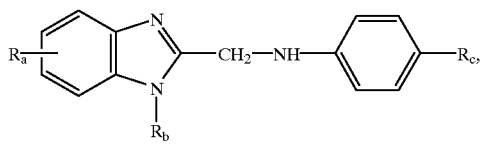

(I)

the tautomers, the stereoisomers, the mixtures thereof, the prodrugs, the derivatives thereof which contain a group which is negatively charged under physiological conditions instead of a carboxy group, and the salts thereof, particularly the physiologically acceptable salts thereof with inorganic or organic acids or bases which have valuable properties.

The compounds of the above general formula I wherein $R_a$ denotes a straight-chained $C_{1-3}$-alkyl group which is substituted in the 1 position by a pyrrolidinocarbonyl or 2,5-dihydropyrrolocarbonyl group optionally substituted by a $C_{1-3}$-alkyl group and by an amino group monosubstituted by a cyano-$C_{1-4}$-alkyl group, and/or $R_c$ denotes a cyano group or a 1,2,4-oxadiazol-3-yl group substituted in the 5 position by a $C_{1-3}$-alkyl or phenyl group, while the phenyl substituent may be substituted by a fluorine, chlorine or bromine atom or by a $C_{1-3}$-alkyl group, are valuable intermediate products for preparing the other compounds of general formula I, and the compounds of the above general formula I wherein $R_c$ denotes one of the following amidino groups, and the tautomers, stereoisomers, mixtures thereof, the prodrugs, the derivatives thereof which contain a group which is negatively charged under physiological conditions instead of a carboxy group, and the salts thereof, particularly the physiologically acceptable salts thereof with inorganic or organic salts, and the stereoisomers thereof, have valuable pharmacological properties, particularly an antithrombotic activity.

In the above general formula $R_a$ denotes a straight-chained $C_{1-3}$-alkyl group wherein the hydrogen atoms may be wholly or partially replaced by fluorine atoms and which is substituted in the 1 position by a pyrrolidinocarbonyl or 2,5-dihydropyrrolocarbonyl group optionally substituted by a $C_{1-3}$-alkyl group and by an amino group which is monosubstituted by a carboxy-$C_{1-4}$-alkyl, cyano-$C_{1-4}$-alkyl or tetrazolyl-$C_{1-4}$-alkyl group, or by a $C_{1-3}$-alkyl group which is terminally substituted by an N-(carboxy-$C_{1-3}$-alkylaminocarbonyl)-amino group optionally substituted by a $C_{1-3}$-alkyl group at one or both amino nitrogen atoms, by a carboxy-$C_{1-3}$-alkoxy, N-(carboxy-$C_{1-3}$-alkyl)-amino, N-($C_{1-3}$-alkyl)-N-(carboxy-$C_{1-3}$-alkyl)-amino, N-(carboxy-$C_{1-3}$-alkylsulphonyl)-amino, N-($C_{1-3}$-alkyl)-N-(carboxy-$C_{1-3}$-alkylsulphonyl)-amino or tetrazolyl-$C_{1-3}$-alkyl group, $R_b$ denotes a $C_{1-3}$-alkyl group and $R_c$ denotes an amidino group, a cyano group or a 1,2,4-oxadiazol-3-yl group substituted in the 5 position by a $C_{1-3}$-alkyl or phenyl group, while the phenyl substituent may be substituted by a fluorine, chlorine or bromine atom or by a $C_{1-3}$-alkyl group.

The carboxy groups, mentioned in the above definition of the groups, may also be replaced by a group which can be converted in vivo into a carboxy group or by a group which is negatively charged under physiological conditions or the amino and imino groups mentioned in the above definition of the groups may also be substituted by a group which can be cleaved in vivo. Such groups are described, for example, in WO 98/46576 and by N. M. Nielson et al. in International Journal of Pharmaceutics 39, 75–85 (1987).

By a group which can be converted in vivo into a carboxy group is meant for example a hydroxymethyl group, a carboxy group esterified with an alcohol wherein the alcoholic moiety is preferably a $C_{1-6}$-alkanol, a phenyl-$C_{1-3}$-alkanol, a $C_{3-9}$-cycloalkanol, whilst a $C_{5-8}$-cycloalkanol may additionally be substituted by one or two $C_{1-3}$-alkyl groups, a $C_{5-8}$-cycloalkanol, wherein a methylene group in the 3 or 4 position is replaced by an oxygen atom or by an imino group optionally substituted by a $C_{1-3}$-alkyl, phenyl-$C_{1-3}$-alkyl, phenyl-$C_{1-3}$-alkoxycarbonyl or $C_{2-6}$-alkanoyl group and the cycloalkanol moiety may additionally be substituted by one or two $C_{1-3}$-alkyl groups, a $C_{4-7}$-cycloalkenol, a $C_{3-5}$-alkenol, a phenyl-$C_{3-5}$-alkenol, a $C_{3-5}$-alkinol or phenyl-$C_{3-5}$-alkinol, with the proviso that no bond to the oxygen atom starts from a carbon atom which carries a double or triple bond, a $C_{3-8}$-cycloalkyl-$C_{1-3}$-alkanol, a bicycloalkanol having a total of 8 to 10 carbon atoms which may additionally be substituted in the bicycloalkyl moiety by one or two $C_{1-3}$-alkyl groups, a 1,3-dihydro-3-oxo-1-isobenzofuranol or an alcohol of formula

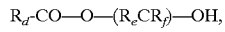

$R_d$-CO—O—($R_e$C$R_f$)—OH, wherein $R_d$ denotes a $C_{1-8}$-alkyl, $C_{5-7}$-cycloalkyl, phenyl or phenyl-$C_{1-3}$-alkyl group, $R_e$ denotes a hydrogen atom, a $C_{1-3}$-alkyl, $C_{5-7}$-cycloalkyl or phenyl group and $R_f$ denotes a hydrogen atom or a $C_{1-3}$-alkyl group, by a group which is negatively charged under physiological conditions is meant a group such as a tetrazol-5-yl, phenylcarbonylaminocarbonyl, trifluoromethylcarbonylaminocarbonyl, $C_{1-6}$-alkylsulphonylamino, phenylsulphonylamino, benzylsulphonylamino, trifluoromethylsulphonylamino, $C_{1-6}$-alkylsulphonylaminocarbonyl, phenylsulphonylaminocarbonyl, benzylsulphonylaminocarbonyl or perfluoro-$C_{1-6}$-alkylsulphonylaminocarbonyl group and by a group which can be cleaved in vivo from an imino or amino group is meant, for example, a hydroxy group, an acyl group such as a benzoyl group optionally mono- or disubstituted by fluorine, chlorine, bromine or iodine atoms or by $C_{1-3}$-alkyl or $C_{1-3}$-alkoxy groups, whilst the substituents may be identical or different, a pyridinoyl group or a $C_{1-16}$-alkanoyl group such as the formyl, acetyl, propionyl, butanoyl, pentanoyl or hexanoyl group, a 3,3,3-trichloropropionyl or allyloxycarbonyl group, a $C_{1-16}$- alkoxycarbonyl or $C_{1-16}$-alkylcarbonyloxy group wherein hydrogen atoms may be wholly or partially replaced by fluorine or chlorine atoms, such as the methoxycarbonyl, ethoxycarbonyl, propoxycarbonyl, isopropoxycarbonyl, butoxycarbonyl, tert. butoxycarbonyl, pentoxycarbonyl, hexoxycarbonyl, octyloxycarbonyl, nonyloxycarbonyl, decyloxycarbonyl, undecyloxycarbonyl, dodecyloxycarbonyl, hexadecyloxycarbonyl, methylcarbonyloxy, ethylcarbonyloxy, 2,2,2-trichloroethylcarbonyloxy, propylcarbonyloxy, isopropylcarbonyloxy, butylcarbonyloxy, tert.butylcarbonyloxy, pentylcarbonyloxy, hexylcarbonyloxy, octylcarbonyloxy, nonylcarbonyloxy, decylcarbonyloxy, undecylcarbonyloxy, dodecylcarbonyloxy or hexadecylcarbonyloxy group, a phenyl-$C_{1-6}$-alkoxycarbonyl group such as the benzyloxycarbonyl, phenylethoxycarbonyl or phenylpropoxycarbonyl group, a 3-amino-propionyl group wherein the amino group may be mono- or disubstituted by $C_{1-6}$-alkyl or $C_{3-7}$-cycloalkyl groups and the substituents may be identical or different, a $C_{1-3}$-alkylsulphonyl-$C_{2-4}$-alkoxycarbonyl, $C_{1-3}$-alkoxy-$C_{2-4}$-alkoxy-$C_{2-4}$-alkoxycarbonyl, $R_d$—CO—O-($R_dCR_f$)—O—CO, $C_{1-6}$-alkyl-CO—NH—($R_gCR_h$)—O—CO or $C_{1-6}$-alkyl-CO—O—($R_gCR_h$)-($R_gCR_h$)—O—CO group wherein $R_d$ to $R_f$ are as hereinbefore defined, $R_g$ and $R_h$, which may be identical or different, denote hydrogen atoms or $C_{1-3}$-alkyl groups.

Furthermore, the saturated alkyl and alkoxy moieties which contain more than 2 carbon atoms mentioned in the above definitions also include the branched isomers thereof such as the isopropyl, tert.butyl, isobutyl group, etc., for example.

Preferred compounds of general formula I mentioned above are those wherein $R_b$ and $R_c$ are as hereinbefore defined and $R_a$ is as hereinbefore defined, with the proviso that one substituent denotes an unbranched $C_{1-3}$-alkyl group or a 2,5-dihydropyrrolocarbonyl group optionally substituted by a $C_{1-3}$-alkyl group, or $R_a$ denotes an ethyl group which is substituted in the 1 position by a pyrrolidinocarbonyl group and by an amino group, while the amino group is substituted by an ethoxycarbonylmethyl group which is substituted in the ethoxy moiety in the 2 position by a methoxy, dimethylamino or tolyl group, by a carboxymethyl, $C_{3-4}$-alkoxycarbonylmethyl, cyclohexyloxycarbonylmethyl, 3-($C_{2-3}$-alkoxycarbonyl)-propyl or tetrazolylmethyl group, $R_b$ denotes a methyl group and $R_c$ denotes an amidino group substituted by a benzoyl, methylbenzoyl, fluorobenzoyl group or trifluoromethylbenzoyl group or $R_a$ denotes an ethyl group which is substituted in the 1 position by a pyrrolidinocarbonyl group substituted in the 2 position by a methyl group and by an amino group, whilst the amino group is substituted by a carboxymethyl or ethoxycarbonylmethyl group, $R_b$ denotes a methyl group and $R_c$ denotes an amidino group or $R_a$ denotes an ethyl group which is substituted in the 1 position by a pyrrolidinocarbonyl group and by an amino group substituted by a carboxymethyl, $C_{3-4}$-alkoxycarbonylmethyl or tetrazolylmethyl group or by a methyl group, whilst the methyl group is substituted by a tetrazolyl, carboxymethoxy, ethoxycarbonylmethoxy, ethoxycarbonylmethylamino, N-(2-carboxyethyl)-N-methylamino, N-[2-($C_{1-3}$-alkoxycarbonyl)-ethyl]-N-methylamino, N-(carboxymethylaminocarbonyl)-N-methyl-amino, N-($C_{1-3}$-alkoxycarbonylmethylaminocarbonyl)-N-methyl-amino, N-(carboxymethylsulphonyl)-N-methyl-amino or N-($C_{1-3}$-alkoxycarbonylmethylsulphonyl)-N-methyl-amino group, $R_b$ denotes a methyl group and $R_c$ denotes an amidino group, the tautomers, the isomers and the salts thereof.

Particularly preferred compounds of the above general formula I are the abovementioned compounds of general formula I with the exception of (1) 2-[4-(N-phenylcarbonyl-amidino)-phenylaminomethyl]-1-methyl-5-[1-(n-butyloxycarbonylmethylamino)-1-(pyrrolidinocarbonyl)-ethyl]-benzimidazole and (2) 2-(4-amidinophenylaminomethyl)-1-methyl-5-[1-(tetrazol-5-yl-methylamino)-1-(pyrrolidinocarbonyl)-ethyl]-benzimidazole, the tautomers, the isomers and the salts thereof.

Most particularly preferred compounds of the above general formula I are those wherein $R_a$ denotes an ethyl group which is substituted in the 1 position by a 2,5-dihydropyrrolocarbonyl group optionally substituted by a methyl group and by an amino group which may be substituted by a $C_{2-4}$-alkoxycarbonyl-$C_{1-4}$-alkyl group wherein the $C_{2-4}$-alkoxy moiety is terminally monosubstituted by a methoxy, dimethylamino, phenyl or tolyl group, by a carboxy-$C_{1-4}$-alkyl, cyclohexyloxycarbonyl-$C_{1-4}$-alkyl or tetrazolyl-$C_{1-4}$-alkyl group, or by a $C_{1-3}$-alkyl group which is terminally substituted by an N-(carboxy-$C_{1-3}$-alkylaminocarbonyl)-amino or N-($C_{1-3}$-alkoxycarbonyl-$C_{1-3}$-alkylaminocarbonyl)-amino group optionally substituted at one or both amino nitrogen atoms by a $C_{1-3}$-alkyl group, by a carboxy-$C_{1-3}$-alkoxy, $C_{1-3}$-alkoxycarbonyl-$C_{1-3}$-alkoxy, N-($C_{1-3}$-alkyl)-N-(carboxy-$C_{1-3}$-alkyl)-amino, N-($C_{1-3}$-alkyl)-N-($C_{1-3}$-alkoxycarbonyl-$C_{1-3}$-alkyl)-amino, N-($C_{1-3}$-alkyl)-N-(carboxy-$C_{1-3}$-alkylsulphonyl)-amino or N-($C_{1-3}$-alkyl)-N-($C_{1-3}$-alkoxycarbonyl-$C_{1-3}$-alkylsulphonyl)-amino or tetrazolyl-$C_{1-3}$-alkyl group, $R_b$ denotes a methyl group and $R_c$ denotes an amidino group optionally substituted by a benzoyl, methylbenzoyl, fluorobenzoyl or trifluoromethylbenzoyl group or $R_a$ denotes an ethyl group which is substituted in the 1 position by a pyrrolidinocarbonyl group and by an amino group, whilst the amino group is substituted by an ethoxycarbonylmethyl group which is substituted in the 2 position by a methoxy, dimethylamino or tolyl group, by a carboxymethyl, propyloxycarbonylmethyl, isopropyloxycarbonylmethyl, isobutyloxycarbonylmethyl, cyclohexyloxycarbonylmethyl, 3-($C_{2-3}$-alkoxycarbonyl)-propyl or tetrazolylmethyl group, $R_b$ denotes a methyl group and R<sub>c</sub> denotes an amidino group substituted by a benzoyl, methylbenzoyl, fluorobenzoyl group or trifluoromethylbenzoyl group or R<sub>a</sub> denotes an ethyl group which is substituted in the 1 position
- by a pyrrolidinocarbonyl group substituted in the 2 position by a methyl group and
- by an amino group, whilst the amino group is substituted by a carboxymethyl or ethoxycarbonylmethyl group, R<sub>b</sub> denotes a methyl group and R<sub>c</sub> denotes an amidino group or R<sub>a</sub> denotes an ethyl group which is substituted in the 1 position
- by a pyrrolidinocarbonyl group and
- by an amino group substituted by a carboxymethyl or $C_{3-4}$-alkoxycarbonylmethyl group or
- by a methyl group, whilst the methyl group is substituted by a tetrazolyl, carboxymethoxy, ethoxycarbonylmethoxy, ethoxycarbonylmethylamino, N-(2-carboxyethyl)-N-methyl-amino, N-[2-($C_{1-3}$-alkoxycarbonyl)-ethyl]-N-methyl-amino, N-(carboxymethylaminocarbonyl)-N-methyl-amino, N-($C_{1-3}$-alkoxycarbonylmethylaminocarbonyl)-N-methyl-amino, N-(carboxymethylsulphonyl)-N-methyl-amino or N-($C_{1-3}$-alkoxycarbonylmethylsulphonyl)-N-methyl-amino group, R<sub>b</sub> denotes a methyl group and R<sub>c</sub> denotes an amidino group, the tautomers, the isomers and the salts thereof.

The following may be mentioned as examples of particularly preferred compounds:

(1) 2-(4-amidinophenylaminomethyl)-1-methyl-5-[1-(ethoxycarbonylmethylamino)-1-(2,5-dihydropyrrolocarbonyl)-ethyl]-benzimidazole, (2) 2-[4-(N-phenylcarbonylamidino)-phenylaminomethyl]-1-methyl-5-[1-(ethoxycarbonylmethylamino)-1-(2,5-dihydropyrrolocarbonyl)-ethyl]-benzimidazole, (3) (R)-2-[4-(N-phenylcarbonylamidino)-phenylaminomethyl]-1-methyl-5-[1-(isobutyloxycarbonylmethylamino)-1-(pyrrolidinocarbonyl)-ethyl]-benzimidazole, (4) (R)-2-[4-(N-phenylcarbonylamidino)-phenylaminomethyl]-1-methyl-5-[1-(n-propyloxycarbonylmethylamino)-1-(pyrrolidinocarbonyl)-ethyl]-benzimidazole, (5) (R)-2-(4-amidinophenylaminomethyl)-1-methyl-5-[1-(carboxymethylamino)-1-[(R,S)-1-methyl-pyrrolidinocarbonyl]-ethyl]-benzimidazole, (6) 2-(4-amidinophenylaminomethyl)-1-methyl-5-[1-(carboxymethylamino)-1-(2,5-dihydropyrrolocarbonyl)-ethyl]-benzimidazole and (7) (R)-2-[4-(N-phenylcarbonylamidino)-phenylaminomethyl]-1-methyl-5-[1-(cyclohexyloxycarbonylmethylamino)-1-(2,5-dihydropyrrolocarbonyl)-ethyl]-benzimidazole, the isomers and the salts thereof.

According to the invention, the compounds of general formula I are obtained by methods known per se, for example by the following methods:

a) In order to prepare a compound of general formula I wherein R<sub>c</sub> denotes a cyano group or a 1,2,4-oxadiazol-3-yl group substituted in the 5 position by a $C_{1-3}$-alkyl or phenyl group, while the phenyl substituent may be substituted by a fluorine, chlorine or bromine atom or by a $C_{1-3}$-alkyl group: cyclising a compound of general formula

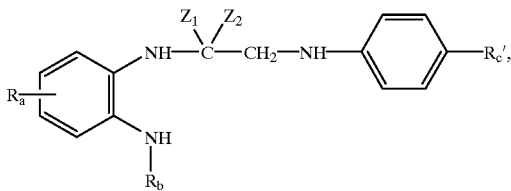

optionally formed in the reaction mixture
wherein
R<sub>a</sub> and R<sub>b</sub> are as hereinbefore defined,
R<sub>c</sub>' denotes a cyano group or a 1,2,4-oxadiazol-3-yl group substituted in the 5 position by a $C_{1-3}$-alkyl or phenyl group, while the phenyl substituent may be substituted by a fluorine, chlorine or bromine atom or by a $C_{1-3}$-alkyl group,
$Z_1$ and $Z_2$, which may be identical or different, denote amino, hydroxy or mercapto groups optionally substituted by alkyl groups with 1 to 6 carbon atoms or
$Z_1$ and $Z_2$ together denote an oxygen or sulphur atom, an imino group optionally substituted by an alkyl group with 1 to 3 carbon atoms, an alkylenedioxy or alkylenedithio group with 2 or 3 carbon atoms.

The cyclisation is conveniently carried out in a solvent or mixture of solvents such as ethanol, isopropanol, glacial acetic acid, benzene, chlorobenzene, toluene, xylene, glycol, glycolmonomethylether, diethyleneglycoldimethylether, sulpholane, dimethylformamide or tetraline or in an excess of the acylating agent used to prepare the compound of general formula II, e.g. in the corresponding nitrile, anhydride, acid halide, ester or amide, for example at temperatures between 0 and 250° C., but preferably at the boiling temperature of the reaction mixture, optionally in the presence of a condensing agent such as phosphorus oxychloride, thionyl chloride, sulphuryl chloride, sulphuric acid, p-toluenesulphonic acid, methanesulphonic acid, hydrochloric acid, phosphoric acid, polyphosphoric acid, acetic acid, acetic anhydride, N,N-dicyclohexyl-carbodiimide or optionally also in the presence of a base such as potassium ethoxide or potassium tert.butoxide. The cyclisation may, however, also be carried out without a solvent and/or condensing agent.

b) In order to prepare a compound of general formula I wherein R<sub>c</sub> denotes an amidino group:
reacting a compound of general formula

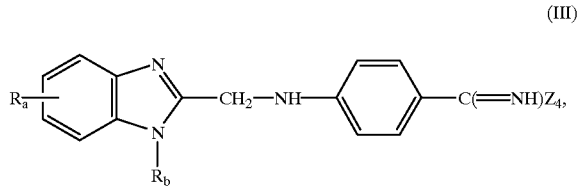

optionally formed in the reaction mixture
wherein
R<sub>a</sub> and R<sub>b</sub> are as hereinbefore defined and
$Z_4$ denotes an alkoxy or aralkoxy group such as the methoxy, ethoxy, n-propoxy, isopropoxy or benzyloxy group or an alkylthio or aralkylthio group such as the methylthio, ethylthio, n-propylthio or benzylthio group, with ammonia or with the salts thereof.

The reaction is conveniently carried out in a solvent such as methanol, ethanol, n-propanol, tetrahydrofuran or dioxane at temperatures between 0 and 150° C., preferably at temperatures between 0 and 80° C., with ammonia or one of its salts such as for example ammonium carbonate or ammonium acetate.

A compound of general formula III is obtained for example by reacting a corresponding cyano compound with a corresponding alcohol such as methanol, ethanol, n-propanol, isopropanol or benzylalcohol in the presence of an acid such as hydrochloric acid or by reacting a corresponding amide with a trialkyloxonium salt such as triethyloxonium-tetrafluoroborate in a solvent such as methylene chloride, tetrahydrofuran or dioxane at temperatures between 0 and 50° C., but preferably at 20° C., or a corresponding nitrile with hydrogen sulphide, conveniently in a solvent such as pyridine or dimethylformamide and in the presence of a base such as triethylamine and subsequent alkylation of the thioamide formed with a corresponding alkyl or aralkyl halide.

c) In order to prepare a compound of general formula I wherein $R_a$ contains a carboxy group and $R_c$ is as hereinbefore defined:

Converting a compound of general formula

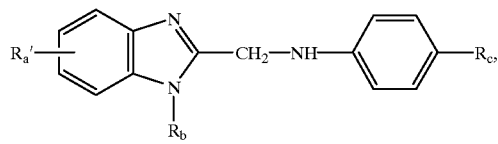

(IV)

wherein $R_b$ and $R_c$ are as hereinbefore defined and $R_a'$ has the meanings given hereinbefore for $R_a$, with the proviso that $R_a$ contains a group which can be converted into a carboxy group by hydrolysis, treatment with an acid or base, thermolysis or hydrogenolysis, by hydrolysis, treatment with an acid or base, thermolysis or hydrogenolysis into a compound of general formula I wherein $R_a$ contains a carboxy group.

A group which may be converted into a carboxy group may be, for example, a carboxyl group protected by a protecting group such as the functional derivatives thereof, e.g. the unsubstituted or substituted amides, esters, thioesters, trimethylsilylesters, orthoesters or iminoesters thereof, which are conveniently converted into a carboxyl group by hydrolysis, the esters thereof with tertiary alcohols, e.g. the tert.butyl ester, which are conveniently converted into a carboxyl group by treatment with an acid or thermolysis, and the esters thereof with aralkanols, e.g. the benzyl ester, which are conveniently converted into a carboxyl group by hydrogenolysis.

The hydrolysis is conveniently carried out either in the presence of an acid such as hydrochloric acid, sulphuric acid, phosphoric acid, acetic acid, trichloroacetic acid, trifluoroacetic acid or the mixtures thereof or in the presence of a base such as lithium hydroxide, sodium hydroxide or potassium hydroxide in a suitable solvent such as water, water/methanol, water/ethanol, water/isopropanol, methanol, ethanol, water/tetrahydrofuran or water/dioxane at temperatures between −10 and 120° C., e.g. at temperatures between room temperature and the boiling temperature of the reaction mixture.

If a compound of formula IV for example contains the tert.butyl or tert.butyloxycarbonyl group, this may also be cleaved by treatment with an acid such as trifluoroacetic acid, formic acid, p-toluenesulphonic acid, sulphuric acid, hydrochloric acid, phosphoric acid or polyphosphoric acid optionally in an inert solvent such as methylene chloride, chloroform, benzene, toluene, diethylether, tetrahydrofuran or dioxane, preferably at temperatures between −10 and 120° C., e.g. at temperatures between 0 and 60° C., or also thermally, optionally in an inert solvent such as methylene chloride, chloroform, benzene, toluene, tetrahydrofuran or dioxane and preferably in the presence of a catalytic amount of an acid such as p-toluenesulphonic acid, sulphuric acid, phosphoric acid or polyphosphoric acid, preferably at the boiling temperature of the solvent used, e.g. at temperatures between 40 and 120° C.

If a compound of formula IV contains the benzyloxy or benzyloxycarbonyl group, for example, this may also be cleaved hydrogenolytically in the presence of a hydrogenation catalyst such as palladium/charcoal in a suitable solvent such as methanol, ethanol, ethanol/water, glacial acetic acid, ethyl acetate, dioxane or dimethylformamide, preferably at temperatures between 0 and 50° C., e.g. at room temperature, and at a hydrogen pressure of 1 to 5 bar.

d) In order to prepare a compound of general formula I wherein $R_c$ denotes an amidino group which is substituted by a group which can be cleaved in vivo:

reacting a compound of general formula

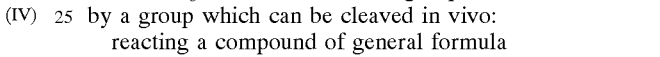

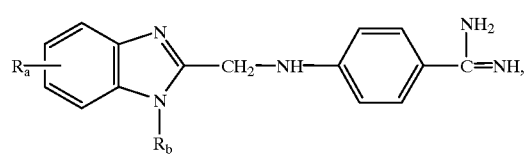

(VI)

wherein $R_a$ and $R_b$ are as hereinbefore defined, with a compound of general formula

$Z_5$-$R_9$ (VII), wherein $R_9$ denotes the acyl group of one of the abovementioned groups which can be cleaved in vivo and $Z_5$ denotes a nucleofugic leaving group such as a halogen atom, e.g. a chlorine, bromine or iodine atom, or a p-nitrophenyl group.

The reaction is preferably carried out in a solvent such as methanol, ethanol, methylene chloride, tetrahydro furan, toluene, dioxane, dimethylsulphoxide or dimethylformamide optionally in the presence of an inorganic or a tertiary organic base, preferably at temperatures between 20° C. and the boiling temperature of the solvent used.

With a compound of general formula VII wherein $Z_5$ denotes a nucleofugic leaving group, the reaction is preferably carried out in a solvent such as methylene chloride, acetonitrile, tetrahydrofuran, toluene, acetone/water, dimethylformamide or dimethylsulphoxide, optionally in the presence of a base such as sodium hydride, potassium carbonate, potassium tert.butoxide or N-ethyldiisopropylamine at temperatures between 0 and 60° C.

e) In order to prepare a compound of general formula I wherein $R_c$ denotes one of the abovementioned amidino groups: catalytic hydrogenation of a compound of general formula

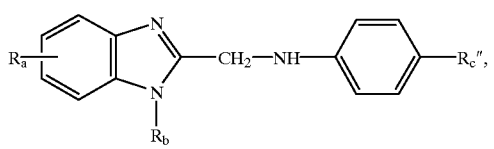

(VIII)

wherein $R_a$ and $R_b$ are as hereinbefore defined and $R_c''$ denotes a 1,2,4-oxadiazol-3-yl group substituted in the 5 position by a $C_{1-3}$-alkyl or phenyl group, wherein the phenyl substituent may be substituted by a fluorine, chlorine or bromine atom or by a $C_{1-3}$-alkyl group, and if necessary subsequent hydrolysis of a compound thus obtained.

The catalytic hydrogenation is preferably carried out in a suitable solvent such as methanol, ethanol, ethanol/water, glacial acetic acid, ethanol/glacial acetic acid, ethyl acetate, dioxane or dimethylformamide in the presence of a hydrogenation catalyst such as palladium/charcoal, preferably at temperatures between 0 and 50° C., e.g. at room temperature, and at a hydrogen pressure of 1 to 5 bar.

The hydrolysis which may follow is conveniently carried out either in the presence of an acid such as hydrochloric acid, sulphuric acid, phosphoric acid, acetic acid, trichloroacetic acid, trifluoroacetic acid or mixtures thereof or in the presence of a base such as lithium hydroxide, sodium hydroxide or potassium hydroxide in a suitable solvent such as water, water/methanol, water/ethanol, water/isopropanol, methanol, ethanol, water/tetrahydrofuran or water/dioxane at temperatures between −10 and 120° C., e.g. at temperatures between room temperature and the boiling temperature of the reaction mixture.

f) In order to prepare a compound of general formula I wherein $R_a$ denotes an amino-$C_{1-3}$-alkyl group in which the amino group is monosubstituted by a carboxy-$C_{1-4}$-alkyl or tetrazolyl-$C_{1-4}$-alkyl group:

alkylating a compound of general formula

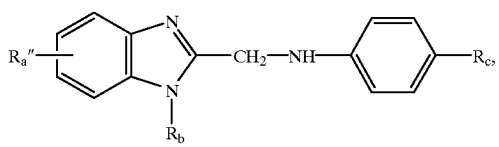

(IX)

wherein $R_b$ and $R_c$ are as hereinbefore defined and $R_a''$ denotes an amino-$C_{1-3}$-alkyl group, with a compound of general formula $R_a'''-Z_7$ (X)

wherein $R_a'''$ denotes a carboxy-$C_{1-4}$-alkyl or tetrazolyl-$C_{1-4}$-alkyl group and $Z_7$ denotes a nucleofugic leaving group such as a halogen atom or a sulphonic acid ester group, e.g. a chlorine, bromine or iodine atom, or a p-nitrophenyl group.

The alkylation is conveniently carried out in a solvent such as methylene chloride, tetrahydrofuran, dioxane, dimethylsulphoxide, dimethylformamide or acetone, optionally in the presence of a reaction accelerator such as sodium or potassium iodide and preferably in the presence of a base such as sodium carbonate or potassium carbonate or in the presence of a tertiary organic base such as N-ethyl-diisopropylamine or N-methyl-morpholine, which may simultaneously also act as solvent, or optionally in the presence of silver carbonate or silver oxide at temperatures between −30 and 100° C., but preferably at temperatures between −10 and 80° C.

If according to the invention a compound of general formula I is obtained wherein $R_a$ contains a carboxy group, this may subsequently be converted by esterification into a corresponding compound wherein $R_a$ contains an esterified carboxy group, and/or if a compound of general formula I is obtained wherein $R_a$ contains an esterified carboxy group, this may subsequently be converted by transesterification into a corresponding compound wherein $R_a$ contains another esterified carboxy group, and/or if a compound of general formula I is obtained wherein $R_a$ contains a cyano group, this may subsequently be converted into a corresponding compound wherein $R_a$ contains a tetrazolyl group.

The subsequent esterification is carried out with a corresponding alcohol, usefully in a solvent or mixture of solvents such as methylene chloride, benzene, toluene, chlorobenzene, tetrahydrofuran, benzene/tetrahydrofuran or dioxane, but preferably in an excess of the alcohol used, optionally in the presence of an acid such as hydrochloric acid or in the presence of a dehydrating agent, e.g. in the presence of isobutyl chloroformate, thionyl chloride, trimethylchlorosilane, hydrochloric acid, sulphuric acid, methanesulphonic acid, p-toluenesulphonic acid, phosphorus trichloride, phosphorus pentoxide, N,N'-dicyclohexyl carbodiimide, N,N'-dicyclohexyl carbodiimide/N-hydroxysuccinimide, N,N'-carbonyldiimidazole or N,N'-thionyldiimidazole, triphenylphosphine/carbon tetrachloride or triphenylphosphine/diethyl azodicarboxylate, optionally in the presence of a base such as potassium carbonate, N-ethyl-diisopropylamine or N,N-dimethylamino-pyridine, conveniently at temperatures between 0 and 150° C., preferably at temperatures between 0 and 80° C., or with a corresponding halide in a solvent such as methylene chloride, tetrahydrofuran, dioxane, dimethylsulphoxide, dimethylformamide or acetone, optionally in the presence of a reaction accelerator such as sodium or potassium iodide and preferably in the presence of a base such as sodium carbonate or potassium carbonate or in the presence of a tertiary organic base such as N-ethyl-diisopropylamine or N-methyl-morpholine, which may also serve as solvent at the same time, or optionally in the presence of silver carbonate or silver oxide at temperatures between −30 and 100° C., but preferably at temperatures between −10 and 80° C.

The subsequent transesterification is carried out with a corresponding alcohol, conveniently in a solvent or mixture of solvents such as methylene chloride, benzene, toluene, chlorobenzene, tetrahydrofuran, benzene/tetrahydrofuran or dioxane, but preferably in an excess of the alcohol used, conveniently in the presence of an acid such as hydrochloric acid or in the presence of a compound such as 2,8,9-trimethyl-1-phospha-2,5,8,9-tetraazabicyclo[3.3.3]undecane at temperatures between 0 and 150° C., preferably at temperatures between 0 and 80° C.

The subsequent conversion of a cyano group into a tetrazolyl group is preferably carried out in a solvent such as benzene, toluene or dimethylformamide at temperatures between 80 and 150° C., preferably at 120 and 130° C. The hydrazoic acid needed is conveniently liberated during the reaction from an alkali metal azide, e.g. from sodium azide, in the presence of a weak acid such as ammonium chloride. The reaction may also take place with another salt or derivative of hydrazoic acid, preferably with aluminium azide or tributyl tin azide, the tetrazole compound optionally obtained in this way being liberated from the salt contained in the reaction mixture by acidification with a dilute acid such as 2N hydrochloric acid or 2N sulphuric acid.

In the reactions described hereinbefore, any reactive groups present such as carboxy, amino or alkylamino groups may be protected during the reaction by conventional protecting groups which are cleaved again after the reaction.

For example, a protecting group for a carboxy group may be a trimethylsilyl, methyl, ethyl, tert.butyl, benzyl or tetrahydropyranyl group and protecting groups for an amino or alkylamino group may be an acetyl, trifluoroacetyl, benzoyl, ethoxycarbonyl, tert.butoxycarbonyl, benzyloxycarbonyl, benzyl, methoxybenzyl or 2,4-dimethoxybenzyl group and additionally, for the amino group, a phthalyl group.

Any protecting group used is optionally subsequently cleaved for example by hydrolysis in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide or by ether cleavage, e.g. in the presence of iodotrimethylsilane, at temperatures between 0 and 100° C., preferably at temperatures between 10 and 50° C.

However, a benzyl, methoxybenzyl or benzyloxycarbonyl group is cleaved hydrogenolytically, for example, with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid at temperatures between 0 and 50° C., but preferably at room temperature, and at a hydrogen pressure of 1 to 7 bar, but preferably 3 to 5 bar.

A methoxybenzyl group may also be cleaved in the presence of an oxidant such as cerium(IV)ammonium nitrate in a solvent such as methylene chloride, acetonitrile or acetonitrile/water at temperatures between 0 and 50° C., but preferably at room temperature.

A 2,4-dimethoxybenzyl group, however, is preferably cleaved in trifluoroacetic acid in the presence of anisol.

A tert.butyl or tert.butyloxycarbonyl group is preferably cleaved by treating with an acid such as trifluoroacetic acid or hydrochloric acid, optionally using a solvent such as methylene chloride, dioxane or ether.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C.

An allyloxycarbonyl group is cleaved by treating with a catalytic amount of tetrakis-(triphenylphosphine)-palladium (O), preferably in a solvent such as tetrahydrofuran and preferably in the presence of an excess of a base such as morpholine or 1,3-dimedone at temperatures between 0 and 100° C., preferably at room temperature and under inert gas, or by treating with a catalytic amount of tris-(triphenylphosphine)-rhodium(I)chloride in a solvent such as aqueous ethanol and optionally in the presence of a base such as 1,4-diazabicyclo[2.2.2]octane at temperatures between 20 and 70° C.

The compounds of general formulae II to X used as starting materials, some of which are known from the literature, are obtained by methods known from the literature, and moreover their preparation is described in the Examples.

The chemistry of the compounds of general formula II is described for example by Jack Robinson in J. Chem. Soc. 1941, 744, that of the benzimidazoles is described by Katritzky and Rees in Comprehensive Heterocyclic Chemistry, Oxford, Pergamon Press, 1984, by Schaumann in Hetarene III, Methoden der organischen Chemie (Houben-Weyl), 4th edition, published by Thieme, Stuttgart 1993.

Thus, for example, a compound of general formula II is obtained by acylating a corresponding o-diamino compound with a corresponding reactive acyl derivative, a compound of general formulae III, IV, VI, VIII and IX is obtained by cyclising a corresponding, substituted compound according to process a) and if necessary subsequently converting a cyano compound thus obtained into the desired starting compound using known methods.

Moreover, the compounds of general formula I obtained may be resolved into their enantiomers and/or diastereomers.

Thus, for example, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)-or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, phosphoric acid, fumaric acid, succinic acid, lactic acid, citric acid, tartaric acid or maleic acid.

Moreover, if the new compounds of formula I contain a carboxy group, they may subsequently, if desired, be converted into the salts thereof with inorganic or organic bases, particularly for pharmaceutical use into the physiologically acceptable salts thereof.

Suitable bases for this purpose include for example sodium hydroxide, potassium hydroxide, cyclohexylamine, ethanolamine, diethanolamine and triethanolamine.

As already mentioned, the new compounds of general formula I and the salts thereof have valuable properties. Thus, the compounds of general formula I wherein $R_c$ denotes a cyano group are valuable intermediate products for preparing the other compounds of general formula I, and the compounds of general formula I wherein $R_c$ denotes one of the amidino groups mentioned hereinbefore, and the tautomers, the stereoisomers and the physiologically acceptable salts thereof have valuable pharmacological properties, particularly an antithrombotic effect which is preferably based on influencing thrombin or factor Xa, e.g. on an inhibitory effect on thrombin or factor Xa, on an effect of prolonging the aPTT time and an inhibitory effect on related serine proteases such as e.g. trypsin, urokinase factor VIIa, factor IX, factor XI and factor XII.

For example, the following compounds:

A=2-(4-amidinophenylaminomethyl)-1-methyl-5-[1-(ethoxycarbonylmethylamino)-1-(2,5-dihydropyrrolocarbonyl)-ethyl]-benzimidazole-dihydrochloride, B=(R)-2-(4-amidinophenylaminomethyl)-1-methyl-5-[1-(carboxymethylamino)-1-[(R,S)-2-methyl-pyrrolidinocarbonyl]-ethyl]-benzimidazole-dihydrochloride and C=(2) 2-(4-amidinophenylaminomethyl)-1-methyl-5-[1-(carboxymethylamino)-1-(2,5-dihydropyrrolocarbonyl)-ethyl]-benzimidazole-dihydrochloride were investigated as follows for their effects on prolonging the aPTT time:

Materials: plasma, from human citrated blood. PTT reagent, Boehringer Mannheim (524298), Calcium solution (0.025 mol/l), Behring Werke, Marburg (ORH 056/57), Diethylbarbiturate acetate buffer, Behring Werke, Marburg (ORWH 60/61), Biomatic B10 coagulometer, Desaga, Wiesloch.

Method:

The aPTT time was determined using a Biomatic B10 coagulometer made by Messrs. Desaga.

The test substance was placed in the test tubes prescribed by the manufacturer together with 0.1 ml of human citrated plasma and 0.1 ml of PTT reagent. The mixture was incubated for three minutes at 37° C. The clotting reaction was started by the addition of 0.1 ml of calcium solution. The time is measured using the apparatus from the addition of the calcium solution up to the clotting of the mixture. Mixtures to which 0.1 ml of DBA buffer were added were used as the controls.

According to the definition, a dosage-activity curve was used to determine the effective concentration of the substance, i.e. the concentration at which the aPTT time is doubled compared with the control.

The Table which follows contains the results found:

| Substance | aPTT time (ED$_{200}$ in μM) |
|---|---|
| A | 0.13 |
| B | 0.12 |
| C | 0.22 |

The compounds prepared according to the invention are well tolerated since no toxic side effects could be detected at therapeutic doses; moreover, the corresponding prodrugs, for example the compounds of Examples 1(6), 2, 3(2) and 3(5), exhibit good oral resorption.

In view of their pharmacological properties the new compounds and the physiologically acceptable salts thereof are suitable for the prevention and treatment of venous and arterial thrombotic diseases, such as for example the treatment of deep leg vein thrombosis, for preventing reocclusions after bypass operations or angioplasty (PT(C)A), and occlusion in peripheral arterial diseases such as pulmonary embolism, disseminated intravascular coagulation, for preventing coronary thrombosis, stroke and the occlusion of shunts. In addition, the compounds according to the invention are suitable for antithrombotic support in thrombolytic treatment, such as for example with rt-PA or streptokinase, for preventing long-term restenosis after PT(C)A, for preventing metastasis and the growth of clot-dependent tumours and fibrin-dependent inflammatory processes, e.g. in the treatment of pulmonary fibrosis.

The dosage required to achieve such an effect is appropriately 0.1 to 30 mg/kg, preferably 0.3 to 10 mg/kg by intravenous route, and 0.1 to 50 mg/kg, preferably 0.3 to 30 mg/kg by oral route, in each case administered 1 to 4 times a day. For this purpose, the compounds of formula I prepared according to the invention may be formulated, optionally together with other active substances, with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The Examples which follow are intended to illustrate the invention:

Example 1

(R)-2-[4-[N-(4-methyl-phenylcarbonyl)-amidino]-phenylamino-methyl]-1-methyl-5-[1-(ethoxycarbonylmethylamino)-1-(pyrrolidinocarbonyl)-ethyl]-benzimidazole a. (R)-5-(4-chloro-3-nitro-phenyl)-5-methyl-imidazolidin-2,4-dione 10.0 g (4.45 mmol) of (R)-5-(4-chlorophenyl)-5-methyl-imidazolidin-2,4-dione are added batchwise to 50 ml of fuming nitric acid at −25 to −35° C. After 45 minutes at −25 to −20° C. the reaction mixture is poured onto ice water. The crystalline product is suction filtered, washed with water and dried.

Yield: 10.5 g (100 % of theory),

Melting point: 173-178° C.

$R_f$ value: 0.30 (silica gel; cyclohexane/ethyl acetate=1: 1)

b. (R)-2-amino-2-(4-chlor-3-nitro-phenyl)-propionic acid 10.5 g (0.044 mol) of (R)-5-(4-chloro-3-nitro-phenyl)-5-methyl-imidazolidine-2,4-dione are refluxed in 200 ml of dioxane and 700 ml of 6N hydrochloric acid for 5 days. The solution is concentrated by evaporation, the residue is taken up in water and extracted with ethyl acetate. The aqueous phase is concentrated by evaporation, mixed with toluene and evaporated to dryness. The residue is triturated with ether, suction filtered and dried.

Yield: 6.8 g (63% of theory), $R_f$ value: 0.24 (Reversed phase RP8, 5% saline solution/methanol=1:1)

c. (R)-2-tert.butyloxycarbonylamino-2-(4-chloro-3-nitro-phenyl)-propionic acid 72.5 g (0.296 mol) of (R)-2-amino-2-(4-chloro-3-nitro-phenyl)-propionic acid are dissolved in 850 ml dioxane and 200 ml water and after the addition of 108.7 ml (0.78 mol) of triethylamine and 136 g (0.623 mol) of di-tert.butyl dicarbonate stirred for 18 hours at room temperature. After the addition of 800 ml of 1N sodium hydroxide solution the solution is stirred for 30 minutes and then extracted 3× with 500 ml of ether. The aqueous phase is adjusted to pH 7 with 1N hydrochloric acid and then to pH 4 with 5% citric acid. After extracting 4 times with 500 ml of ethyl acetate, the combined organic phases are washed with water, dried, suction filtered through magnesium sulphate and concentrated by evaporation.

Yield: 86.8 g (85 % of theory), $R_f$ value: 0.3 (silica gel; methylene chloride/methanol 4:1+1% ammonia)

$C_{14}H_{17}ClN_2O_6$ (344.7)

Mass spectrum: $(M-H)^-$=343 d. (R)-2-tert.butyloxycarbonylamino-2-(4-methylamino-3-nitro-phenyl)-propionic acid 96 g (0.278 mol) of (R)-2-tert.butyloxycarbonylamino-2-(4-chloro-3-nitro-phenyl)propionic acid and 440 ml of methylamine solution (40% solution in water) are heated to 90° C. in a pressurised vessel for seven hours. After cooling, the reaction solution is adjusted to pH 3.5 by the addition of glacial acetic acid, whilst cooling with ice, and extracted with ethyl acetate. After the solvent has been evaporated off, the residue remaining is washed with ether and dried.

Yield: 70 g (74 % of theory), $R_f$ value: 0.30 (silica gel; methylene chloride/ethanol= 19:1+1% glacial acetic acid)

$C_{15}H_{21}N_3O_6$ (339.3)

Mass spectrum: $(M-H)^-$=338 e. (R)-2-(4-methylamino-3-nitro-phenyl)-2-tert.butyloxycarbonylamino-1-pyrolidino-propanone 50 g (0.147 mol) of (R)-2-tert.butyloxycarbonylamino-2-(4-methylamino-3-nitro-phenyl)propionic acid are dissolved in 275 ml of dimethylformamide and after the addition of 47.5 g (0.147 mol) of O-(benzotriazol-1-yl)-N,N,N',N'-tetramethyluronium tetrafluoroborate, 24.5 g (0.334 mol) of pyrrolidine and 30 ml of (0.273 mol) of N-methyl-morpholine the mixture is stirred for 20 hours at room temperature. The solution is poured onto ice water and acidified with citric acid (pH 5-6). The precipitate formed is suction filtered, washed with water and dried.

Yield: 45.5 g (79% of theory), $R_f$ value: 0.6 (silica gel; petroleum ether/ethyl acetate= 1:1)

f. (R)-2-(4-methylamino-3-amino-phenyl)-2-tert.butyloxycarbonylamino-1-pyrrolidino-propanone 25.5 g (65 mmol) of (R)-2-(4-methylamino-3-nitro-phenyl)-2-tert.butyloxycarbonylamino-1-pyrrolidino-propanone are dissolved in 650 ml of methanol and after the addition of 4.0 g of palladium on activated charcoal (20%) the mixture is hydrogenated for 2 hours at room temperature. Then the catalyst is filtered off and concentrated by evaporation.

Yield: 21.4 g (91% of theory), $R_f$ value: 0.31 (silica gel; ethyl acetate+1% ammonia)

g. (R)-2-[4-methylamino-3-(4-cyanophenylaminomethylcarbonylamino)-phenyl]-2-tert.butyloxycarbonylamino-1-pyrrolidino-propanone Prepared analogously to Example 1e from (R)-2-(4-methylamino-3-amino-phenyl)-2-tert.butyloxycarbonylamino-1-pyrrolidino-propanone, O-(benzotriazol-1-yl)-N,N,N',N'-tetramethyluroniumtetrafluoroborate, 4-cyanophenylglycine and N-methyl-morpholine in dimethylformamide.

Yield: 100% of theory, $R_f$ value: 0.47 (silica gel; ethyl acetate)

h. (R)-2-(4-cyanophenylaminomethyl)-1-methyl-5-[1-(N-tert.butyloxycarbonylamino)-1-(pyrrolidinocarbonyl)-ethyl]-benzimidazole 47.7 g (0.042 mol) of (R)-2-[4-methylamino-3-(4-cyanophenylamino-methylcarbonylamino)-phenyl]-2-tert.butyloxycarbonylamino-1-pyrrolidino-propanone are refluxed in 300 ml of glacial acetic acid for 2 hours. The reaction mixture is added to ice water and adjusted to pH 8 with conc. ammonia. The precipitate formed is filtered off, washed with water and dried.

Yield: 46 g (100 % of theory), $R_f$ value: 0.3 (silica gel; ethyl acetate+1% ammonia)

i. (R)-2-(4-cyanophenylaminomethyl)-1-methyl-5-[1-amino-1-(pyrrolidinocarbonyl)-ethyl]-benzimidazole 25.1 g (50 mmol) of (R)-2-(4-cyanophenylaminomethyl)-1-methyl-S-[1-(N-tert.butyloxycarbonylamino)-1-(pyrrolidinocarbonyl)-ethyl]-benzimidazole are dissolved in 500 ml of 6N hydrochloric acid at 35° C. and stirred for one hour at this temperature. The solution is mixed with ice, made alkaline with ammonia and extracted with ethyl acetate. The combined organic extracts are dried and concentrated by evaporation.

Yield: 17.8 g (88% of theory), $R_f$ value: 0.5 (silica gel; methylene chloride/ethanol=4:1+ 1% ammonia)

k. (R)-2-(4-cyanophenylaminomethyl)-1-methyl-5-(1-ethoxycarbonylmethylamino)-1-(pyrrolidinocarbonyl)-ethyl]-benzimidazole 4.2 g (10.44 mmol) of (R)-2-(4-cyanophenylaminomethyl)-1-methyl-5-[1-amino-1-(pyrrolidinocarbonyl)-ethyl]-benzimidazole are dissolved in 100 ml of acetone and combined with 2.3 g (16.65 mmol) of potassium carbonate and 2.25 ml (20.2 mmol) of ethyl bromoacetate. The suspension is heated to 60° C. for 5 hours. After cooling the reaction mixture is stirred into 400 ml of ice water, the precipitate formed is filtered off, washed with water and dried. The crude product is chromatographed on silica gel, eluting with methylene chloride/ethanol (19:1 and 9:1). The uniform fractions are combined and concentrated by evaporation.

Yield: 3.1 g (61% of theory), $R_f$ value: 0.4 (silica gel; ethyl acetate/ethanol=9:1)

l. (R)-2-(4-amidinophenylaminomethyl)-1-methyl-5-[1-(1-ethoxycarbonylethylamino)-1-(pyrrolidinocarbonyl)-ethyl]-benzimidazole-hydrochloride 6.8 g (13.8 mmol) of (R)-2-(4-cyanophenylaminomethyl)-1-methyl-5-[1-ethoxycarbonylmethylamino)-1-(pyrrolidinocarbonyl)-ethyl]-benzimidazole are dissolved in 400 ml of saturated ethanolic hydrochloric acid and stirred for 23 hours at room temperature. The solvent is distilled off, the residue is dissolved in 200 ml of absolute ethanol and combined with 20 g (0.21 mol) of ammonium carbonate. After 20 hours at room temperature 100 ml of ethanol are added and after another 10 hours' stirring at room temperature the mixture is filtered and evaporated to dryness. The residue is stirred in 200 ml of acetone, filtered off, washed with ether and dried.

Yield: 7.6 g (100% of theory), $R_f$ value: 0.61 (Reversed phase RP8; 5% sodium chloride solution/methanol=3:2)

$C_{27}H_{36}N_7O_3 \times HCl$ (505.64/542.09)

Mass spectrum: $(M+H)^+=506$ m. (R)-2-[4-[N-(4-methyl-phenylcarbonyl)-amidino]-phenylaminomethyl]-1-methyl-5-[1-(ethoxycarbonylmethylamino)-1-(pyrrolidinocarbonyl)-ethyl]-benzimidazole A suspension of 0.7 g (1.2 mmol) of (R)-2-(4-amidinophenylaminomethyl)-1-methyl-5-[1-(ethoxycarbonylmethylamino)-1-(pyrrolidinocarbonyl)-ethyl]-benzimidazole-dihydrochloride in 25 ml of methylene chloride is combined with 4.0 ml (28 mmol) of triethylamine and 0.8 g (3.0 mmol) of 4-nitrophenyl 4-methyl-benzoate and heated to 50° C. for 3.5 hours, whereupon a clear solution is formed. After cooling, it is washed with sodium bicarbonate solution, saline solution and water, dried over magnesium sulphate and concentrated by evaporation. The crude product is purified on silica gel, eluting with ethyl acetate/ethanol (50:1 and 9:1). The uniform fractions are combined, concentrated by evaporation, triturated with ether, suction filtered and dried.

Yield: 0.5 g (66% of theory), $R_f$ value: 0.50 (silica gel; ethyl acetate/ethanol=9:1)

$C_{35}H_{41}N_7O_4$ (623.75)

Mass spectrum: $(M+H)^+=624$ $(M+Na)^+=646$ $(M-H)^-=622$

The following compounds are obtained analogously to Example 1:

(1) (R)-2-(4-amidinophenylaminomethyl)-1-methyl-5-[1-(isopropyloxycarbonylmethylamino)-1-(pyrrolidinocarbonyl)-ethyl]-benzimidazole-acetate Yield: 69% of theory, $R_f$ value: 0.2 (silica gel; methylene chloride/ethanol=7:3+1% glacial acetic acid)

$C_{28}H_{37}N_7O_3 \times CH_3COOH$ (519.65/579.70)

Mass spectrum: $(M+H)^+=520$ $(M-H)^-=518$ (2) (R)-2-[4-[N-(4-fluorophenylcarbonyl)amidino]-phenylaminomethyl]-1-methyl-5-[1-(ethoxycarbonylmethylamino)-1-(pyrrolidinocarbonyl)-ethyl]-benzimidazole Yield: 40% of theory, $R_f$ value: 0.4 (silica gel; ethyl acetate/ethanol=9:1+1% ammonia)

$C_{34}H_{38}FN_7O_4$ (627.72)

Mass spectrum: $(M+H)^+=628$ $(M+Na)^+=650$ $(M-H)^-=626$ (3) (R)-2-[4-[N-(4-trifluoromethyl-phenylcarbonyl) amidino]-phenylaminomethyl]-1-methyl-5-[1-(ethoxycarbonylmethylamino)-1-(pyrrolidinocarbonyl)-ethyl]-benzimidazole Yield: 47% of theory, $R_f$ value: 0.53 (silica gel; methylene chloride/methanol/conc. ammonia=9:0.9:0.1)

$C_{35}H_{38}F_3N_7O_4$ (677.73)

Mass spectrum: $(M+H)^+=678$ $(M+Na)^+=700$ $(M-H)^-=676$ (4) (R)-2-[4-(N-phenylcarbonylamidino)-phenylaminomethyl]-1-methyl-5-[1-(tetrazol-5-yl-methylamino)-1-(pyrrolidinocarbonyl)-ethyl]-benzimidazole (5) 2-(4-amidinophenylaminomethyl)-1-methyl-5-[1-(ethoxycarbonylmethylamino)-1-(2,5-dihydropyrrolocarbonyl)-ethyl]-benzimidazole-dihydrochloride Yield: 94% of theory, $R_f$ value: 0.2 (Reversed phase RP8; 5% saline solution/methanol2:3)

$C_{27}H_{33}N_7O_3 \times 2$ HCl (503.6/576.51)

Mass spectrum: $(M+H)^+=504$ $(M-H+HCl)^-=538/540$ (Cl)

(6) 2-[4-(N-phenylcarbonylamidino)-phenylaminomethyl]-1-methyl-5-[1-(ethoxycarbonylmethylamino)-1-(2,5-dihydropyrrolocarbonyl)-ethyl]-benzimidazole Yield: 71% of theory, $R_f$ value: 0.3 (silica gel; ethyl acetate/ethanol=9:1)

$C_{34}H_{37}N_7O_4$ (607.72)

Mass spectrum: $(M+H)^+=608$ $(M+Na)^+=630$ $(M-H)^-=606$ (7) (R)-2-(4-amidinophenylaminomethyl)-1-methyl-5-[1-(ethoxycarbonylmethylamino)-1-[(R,S)-1-methyl-pyrrolidinocarbonyl]-ethyl]-benzimidazole-dihydrochloride (mixture of diastereomers)

Yield: 88% of theory, $R_f$ value: 0.3 (Reversed phase RP8; 5% saline solution/methanol=3:2)

$C_{28}H_{37}N_7O_3 \times 2$ HCl (519.65/592.56)

Mass spectrum: $(M+H)^+=520$ $(M+Cl)^-554/6$ (Cl)

(8) (R)-2-[4-(N-phenylcarbonylamidino)-phenylaminomethyl]-1-methyl-5-[1-(3-ethoxycarbonyl-propylamino)-1-(pyrrolidinocarbonyl)-ethyl]-benzimidazole Yield: 19% of theory, $R_f$ value: 0.44 (silica gel; methylene chloride/methanol=4:1+1% glacial acetic acid)

$C_{36}H_{43}N_7O_4$ (637.79)

Mass spectrum: $(M+H)^+=638$ $(M-H)^-=636$ (9) (R)-2-[4-(N-n-hexyloxycarbonylamidino)-phenylaminomethyl]-1-methyl-5-[1-(n-propyloxycarbonylmethylamino)-1-(pyrrolidinocarbonyl)-ethyl]-benzimidazole Yield: 70% of theory, $R_f$ value: 0.37 (silica gel; ethyl acetate/ethanol=9:1)

$C_{35}H_{49}N_7O_5$ (647.82)

Mass spectrum: $(M+Na)^+=670$ $(M-H)^-=646$

Example 2

(R)-2-[4-(N-phenylcarbonylamidino)-phenylaminomethyl]-1-methyl-5-[1-(n-butyloxycarbonylmethylamino)-1-(pyrrolidinocarbonyl)-ethyl]-benzimidazole A solution of 0.3 g (0.53 mmol) of (R)-2-[4-(N-phenylcarbonylamidino)-phenylaminomethyl]-1-methyl-5-[1-(ethoxycarbonylmethylamino)-1-(pyrrolidinocarbonyl)-ethyl]-benzimidazole in 5 ml of n-butanol is mixed with 0.1 g (0.46 mmol) of 2,8,9-trimethyl-1-phospha-2,5,8,9-tetraazabicyclo[3.3.3]undecane and stirred for 1 hour at room temperature. The reaction mixture is purified on silica gel, eluting with ethyl acetate/ethanol/conc. ammonia (50:0.95:0.05 and 20:0.95:0.05). The uniform fractions are combined and concentrated by evaporation.

Yield: 0.19 g (57% of theory), $R_f$ value: 0.45 (silica gel; ethyl acetate/ethanol=9:1+1% ammonia)

$C_{36}H_{43}N_7O_4$ (637.78)

Mass spectrum: $(M+H)^+=638$ $(M+Na)^+=660$ $(M-H)^-=636$

The following compounds are obtained analogously to Example 2:

(1) (R)-2-[4-(N-phenylcarbonylamidino)-phenylaminomethyl]-1-methyl-5-[1-(isobutyloxycarbonylmethylamino)-1-(pyrrolidinocarbonyl)-ethyl]-benzimidazole Yield: 16% of theory, $R_f$ value: 0.48 (silica gel; ethyl acetate/ethanol=9:1+1% ammonia)

$C_{36}H_{43}N_7O_4$ (637.78)

Mass spectrum: $(M+H)^+=638$ $(M+Na)^+=660$ $(M-H)^-=636$ (2) (R)-2-[4-(N-phenylcarbonylamidino)-phenylaminomethyl]-1-methyl-5-[1-(2-methoxy-ethyloxycarbonylmethylamino)-1-(pyrrolidinocarbonyl)-ethyl]-benzimidazole Yield: 43% of theory, $R_f$ value: 0.31 (silica gel; ethyl acetate/ethanol=9:1+1% ammonia)

$C_{35}H_{41}N_7O_5$ (639.76)

Mass spectrum: $(M+H)^+=640$ $(M-H)^-=638$ (3) (R)-2-[4-(N-phenylcarbonylamidino)-phenylaminomethyl]-1-methyl-5-[1-(2-dimethylamino-ethyloxycarbonylmethylamino)-1-(pyrrolidinocarbonyl)-ethyl]-benzimidazole Yield: 23% of theory, $R_f$ value: 0.26 (silica gel; methylene chloride/methanol/ammonia=9:0.9:0.1)

$C_{36}H_{44}N_8O_4$ (652.8)

Mass spectrum: $(M+H)^+=651$ $(M-H)^-=653$ (4) (R)-2-[4-(N-phenylcarbonylamidino)-phenylaminomethyl]-1-methyl-5-[1-(2-(2-methylphenyl)-ethyloxycarbonylmethylamino)-1-(pyrrolidinocarbonyl)-ethyl]-benzimidazole Yield: 23% of theory, $R_f$ value: 0.52 (silica gel; ethyl acetate/ethanol/ammonia=9:0.95:0.05)

$C_{41}H_{45}N_7O_4$ (699.86)

Mass spectrum: $(M+H)^+=700$ $(M+Na)^+=722$ $(M-H)^-=698$ (5) (R)-2-[4-(N-phenylcarbonylamidino)-phenylaminomethyl]-1-methyl-5-[1-(cyclohexyloxycarbonylmethylamino)-1-(pyrrolidinocarbonyl)-ethyl]-benzimidazole Yield: 34% of theory, $R_f$ value: 0.49 (silica gel; ethyl acetate/ethanol=9:1+1% ammonia)

$C_{38}H_{47}N_7O_4$ (663.83)

Mass spectrum: $(M+H)^+=664$ $(M+Na)^+=686$ $(M-H)^-=662$

Example 3

(R)-2-[4-(N-phenylcarbonylamidino)-phenylaminomethyl]-1-methyl-5-[1-(isopropyloxycarbonylmethylamino)-1-(2,5-dihydropyrrolocarbonyl)-ethyl]-benzimidazole 2.1 ml of conc. sulphuric acid are added dropwise to a solution of 0.5 g (0.82 mmol) of (R)-2-[4-(N-phenylcarbonylamidino)-phenylaminomethyl]-1-methyl-5-[1-(ethoxycarbonylmethylamino)-1-(2,5-dihydropyrrolocarbonyl)-ethyl]-benzimidazole in 12.3 ml of isopropanol. After 4 hours at 85° C. the solution is cooled and poured onto 250 ml of ice water. The pH is adjusted to 8.5 by the addition of conc. ammonia. The precipitate formed is suction filtered, dried and purified on silica gel, eluting with methylene chloride+2% methanol+0.01% ammonia. The uniform fractions are combined and concentrated by evaporation, the residue is triturated with ether, filtered off and dried.

Yield: 0.19 g (37% of theory), $R_f$ value: 0.46 (silica gel; ethyl acetate/ethanol=9:1+1% ammonia)

$C_{35}H_{39}N_7O_4$ (621.75)

Mass spectrum: $(M+H)^+=622$ $(M+Na)^+=644$ $(M-H)^-=620$

The following compounds are obtained analogously to Example 3:

(1) (R)-2-[4-(N-phenylcarbonylamidino)-phenylaminomethyl]-1-methyl-5-[1-(n-propyloxycarbonylmethylamino)-1-(2,5-dihydropyrrolocarbonyl)-ethyl]-benzimidazole Yield: 33% of theory, $R_f$ value: 0.46 (silica gel; ethyl acetate/ethanol=9:1+1% ammonia)

$C_{35}H_{39}N_7O_4$ (621.75)

Mass spectrum: $(M+H)^+=622$ $(M+Na)^+=644$ $(M-H)^-=620$ (2) (R)-2-[4-(N-phenylcarbonylamidino)-phenylaminomethyl]-1-methyl-5-[1-(n-propyloxycarbonylmethylamino)-1-(pyrrolidinocarbonyl)-ethyl]-benzimidazole Yield: 36% of theory, $R_f$ value: 0.45 (silica gel; ethyl acetate/ethanol=9:1+1% ammonia)

$C_{35}H_{41}N_7O_4$ (623.76)

Mass spectrum: $(M+H)^+=624$ $(M+Na)^+=646$ $(M-H)^-=622$ (3) (R)-2-(4-amidinophenylaminomethyl)-1-methyl-5-[1-(n-butyl-oxycarbonylmethylamino)-1-(pyrrolidinocarbonyl)-ethyl]-benzimidazole-dihydrochloride Yield: 8% of theory, $R_f$ value: 0.44 (silica gel; methylene chloride/methanol=4:1+1% ammonia)

$C_{29}H_{39}N_7O_3 \times 2$ HCl (533.69/606.6)

Mass spectrum: $(M+H)^+=534$ $(M-H)^-=532$ (4) (R)-2-(4-amidinophenylaminomethyl)-1-methyl-5-[1-(n-propyloxycarbonylmethylamino)-1-(pyrrolidinocarbonyl)-ethyl]-benzimidazole-sulphate Yield: 7% of theory, $R_f$ value: 0.36 (silica gel; methylene chloride/methanol=4:1+1% ammonia)

$C_{28}H_{37}N_7O_3 \times H_2SO_4$ (519.65/617.7)

Mass spectrum: $(M+H)^+=520$ (5) (R)-2-[4-(N-phenylcarbonylamidino)-phenylaminomethyl]-1-methyl-5-[1-(cyclohexyloxycarbonylmethylamino)-1-(2,5-dihydropyrrolocarbonyl)-ethyl]-benzimidazole Yield: 22% of theory, $R_f$ value: 0.60 (silica gel; ethyl acetate/ethanol=9:1+1% ammonia)

$C_{38}H_{43}N_7O_4$ (661.81)

Mass spectrum: $(M+H)^+=662$ $(M+Na)^+=684$ $(M-H)^-=660$ (6) (R)-2-[4-(N-phenylcarbonylamidino)-phenylaminomethyl]-1-methyl-5-[1-(3-(isopropyloxycarbonyl)-propylamino)-1-(pyrrolidinocarbonyl)-ethyl]-benzimidazole (7) (R)-2-[4-(N-phenylcarbonylamidino)-phenylaminomethyl]-1-methyl-5-[1-(3-(n-propyloxycarbonyl)-propylamino)-1-(pyrrolidinocarbonyl)-ethyl]-benzimidazole Example 4

(R)-2-(4-amidinophenylaminomethyl)-1-methyl-5-[1-(tetrazol-5-yl-methylamino)-1-(pyrrolidinocarbonyl)-ethyl]-benzimidazole a. 4-(5-methyl-1,2,4-oxadiazol-3-yl)-phenylamino-ethyl acetate Prepared analogously to Example 1k from 4-(5-methyl-1,2,4-oxadiazol-3-yl)-aniline and ethyl bromoacetate in N-ethyl-diisopropylamine.

Yield: 78% of theory, $R_f$ value: 0.60 (silica gel; ethyl acetate/petroleum ether=1:1)

b. 4-(5-methyl-1,2,4-oxadiazol-3-yl)-phenyl-N-tert.butyloxycarbonylamino-ethyl acetate Prepared analogously to Example 1c from 4-(5-methyl-1,2,4-oxadiazol-3-yl)-phenylaminoethyl acetate and di-tert.butyldicarbonate/N-ethyl-diisopropylamine in dioxane.

Yield: 63% of theory, $R_f$ value: 0.48 (silica gel; ethyl acetate/cyclohexane=1:2)

c. 4-(5-methyl-1.2.4-oxadiazol-3-yl)-phenyl-N-tert.butyloxycarbonyl-aminoacetic acid A solution of 3.5 g (9.7 mmol) of 4-(5-methyl-1,2,4-oxadiazol-3-yl)-phenyl-N-tert.butyloxycarbonylamino-ethyl acetate in 10 ml of tetrahydrofuran and 4 ml of methanol is combined with 9.7 ml of 1N sodium hydroxide solution (9.7 mmol) and stirred for 3 hours at room temperature. The reaction mixture is evaporated down to half its volume and mixed with water. The pH value is adjusted to 4-5 by the addition of glacial acetic acid, the precipitate formed is filtered off, washed with water and dried.

Yield: 2.8 g (87% of theory), $R_f$ value: 0.5 (Reversed phase RP8; 5% saline solution/methanol=1:3)

d. (R)-2-[4-(5-methyl-1.2.4-oxadiazol-3-yl)-phenyl-N-tert.butyloxycarbonyl-aminomethyl]-1-methyl-5-[2-tert.butyloxycarbonylamino-1-(pyrrolidinocarbonyl)-ethyl]-benzimidazole Prepared analogously to Example 1g/h from (R)-2-(4-methylamino-3-amino-phenyl)-2-tert.butyloxycarbonylamino-1-pyrrolidino-propanone, 4-(5-methyl-1,2,4-oxadiazol-3-yl)-phenyl-N-tert.butyloxycarbonyl-aminoacetic acid and carbonyldiimidazole in tetrahydrofuran and subsequently treated with glacial acetic acid.

Yield: 47% of theory, $R_f$ value: 0.46 (silica gel; ethyl acetate)

e. (R)-2-[4-(5-methyl-1.2.4-oxadiazol-3-yl)-phenylaminomethyl]-1-methyl-5-[1-amino-1-(pyrrolidinocarbonyl)-ethyl]-benzimidazole Prepared analogously to Example 1i from (R)-2-[4-(5-methyl-1,2,4-oxadiazol-3-yl)-phenyl-N-tert.butyloxycarbonyl-aminomethyl]-1-methyl-5-[2-tert.butyloxycarbonyl-amino-1-(pyrrolidino-carbonyl)-ethyl]-benzimidazole and 6N hydrochloric acid.

Yield: 91% of theory, $R_f$ value: 0.44 (silica gel; methylene chloride/methanol/ammonia=9:0.9:0.1)

f. (R)-2-[4-(5-methyl-1,2,4-oxadiazol-3-yl)-phenylaminomethyl]-1-methyl-5-[1-cyanomethylamino-1-(pyrrolidinocarbonyl)-ethyl]-benzimidazole Prepared analogously to Example 1k from (R)-2-[4-(5-methyl-1,2,4-oxadiazol-3-yl)-phenylaminomethyl]-1-methyl-5-[1-amino-1-(pyrrolidinocarbonyl)-ethyl]-benzimidazole and bromoacetonitrile/potassium carbonate in acetone.

Yield: 72% of theory, $R_f$ value: 0.54 (silica gel; ethyl acetate/ethanol=9:1+1% ammonia)

$C_{27}H_{30}N_8O_2$ (498.59)

Mass spectrum: $(M+H)^+=499$ $(M-H)^-=497$ $(M+Na)^+=521$ g. (R)-2-[4-(5-methyl-1,2,4-oxadiazol-3-yl)-phenylaminomethyl]-1-methyl-5-[1-(tetrazol-5-yl-methylamino)-1-(pyrrolidinocarbonyl)-ethyl]-benzimidazole 1.1 g (2.2 mmol) of (R)-2-[4-(5-methyl-1,2,4-oxadiazol-3-yl)-phenylaminomethyl]-1-methyl-5-[1-cyanomethylamino-1-(pyrrolidinocarbonyl)-ethyl]-benzimidazole are suspended in 20 ml of toluene and 60 ml of dioxane and combined with 2.2 g (6.6 mmol) of tributyl tin azide. The reaction mixture is heated to 130° C. for 6 hours. After the solvent has been evaporated off, the residue is triturated with petroleum ether, filtered, washed with petroleum ether and dried. The crude product is purified on silica gel, eluting with methylene chloride/methanol 20:1 and 9:1. The uniform fractions are combined and concentrated by evaporation.

Yield: 0.7 g (59% of theory)

$R_f$ value: 0.33 (silica gel; methylene chloride:methanol=9:1)

$C_{27}H_{31}N_{11}O_2$ (541.6)

Mass spectrum: $(M-H)^-=540$ $(M+Na)^+=564$ h. (R)-2-(4-amidinophenylaminomethyl)-1-methyl-5-[1-(tetrazol-5-yl-methylamino)-1-(pyrrolidinocarbonyl)-ethyl]-benzimidazole Prepared analogously to Example 1h from (R)-2-[4-(5-methyl-1,2,4-oxadiazol-3-yl)-phenylaminomethyl]-1-methyl-5-[1-(tetrazol-5-yl-methylamino)-1-(pyrrolidinocarbonyl)-ethyl]-benzimidazole and hydrogen/palladium (20% on activated charcoal) in ethanol/glacial acetic acid.

Yield: 63% of theory, $R_f$ value: 0.35 (Reversed phase RP8; 5% saline solution/methanol=4:3)

$C_{25}H_{31}N_{11}O$ (501.6)

Mass spectrum: $(M+H)^+=502$ $(M-H)^-=500$

Example 5

2-(4-amidinophenylaminomethyl)-1-methyl-5-[1-(ethoxycarbonylmethyloxymethyl)-1-(pyrrolidinocarbonyl)-ethyl]-benzimidazole-acetate a. methyl 2-(4-chloro-phenyl)-3-hydroxy-2-methyl-propionate 35 ml of a 1.6 molar solution of n-butyllithium in hexane (61 mmol) are added dropwise to a solution of 8.1 ml of diisopropylamine (85 mmol) in 20 ml of tetrahydrofuran at −78° C. Then a solution of 10.0 g (50 mmol) of methyl 2-(4-chloro-phenyl)-propionate in 30 ml of tetrahydrofuran is added dropwise at −78° C. Gaseous formaldehyde is piped into the reaction mixture at −20° C. for 30 minutes. After the addition of 5% citric acid and glacial acetic acid the mixture is extracted with ethyl acetate. The organic phases are washed with 1N sulphuric acid, water, saturated sodium bicarbonate solution and saline solution and dried over magnesium sulphate. The crude product is purified on silica gel, eluting with cyclohexane/ethyl acetate (19:1; 9:1; 4:1; 1:1 and 0:1). The uniform fractions are combined and concentrated by evaporation.

Yield: 9.7 g of yellow oil (84% of theory), $R_f$ value: 0.25 (silica gel; petroleum ether/ethyl acetate= 4:1)

b. 2-(4-chloro-phenyl)-3-hydroxy-2-methyl-propionic acid

Prepared analogously to Example 8 from methyl 2-(4-chloro-phenyl)-3-hydroxy-2-methyl-propionate and sodium hydroxide solution in ethanol.

Yield: 83% of theory, $R_f$ value: 0.55 (silica gel; ethyl acetate/cyclohexane=2:1+ 1% glacial acetic acid)

c. 2-(4-chloro-3-nitro-phenyl)-2-methyl-3-nitroxy-propionic acid

Prepared analogously to Example 1a from 2-(4-chloro-phenyl)-3-hydroxy-2-methyl-propionic acid and nitric acid.

Yield: 90% of theory,

Melting point: 129-132° C.

$C_{10}H_9ClN_2O_7$ (304.64)

d. 2-(4-chloro-3-nitro-phenyl)-2-methyl-3-hydroxy-propionic acid

Prepared analogously to Example 1i from 2-(4-chloro-3-nitro-phenyl)-3-nitroxy-2-methyl-propionic acid and 6N hydrochloric acid in dioxane.

Yield: 98% of theory, $C_{10}H_{10}ClNO_5$ (259.65)

Mass spectrum: $(M−H)^−$=258/60 (Cl) $(2M−H)^−$=517/9 ($Cl_2$)

e. 2-[4-(N-benzyl-methylamino)-3-nitro-phenyl]-2-methyl-3-hydroxy-propionic acid Prepared analogously to Example 1e from 2-(4-chloro-3-nitro-phenyl)-3-hydroxy-2-methyl-propionic acid and N-methyl-benzylamine.

Yield: 81% of theory, $C_{18}H_{20}ClN_2O_5$ (344.37)

Mass spectrum: $M^+$=344 f. 2-[4-(N-benzyl-methylamino)-3-nitro-phenyl]-2-methyl-3-hydroxy-1-pyrrolidin-1-yl-propan-1-one Prepared analogously to Example 1e from 2-[4-(N-benzyl-methylamino)-3-nitro-phenyl]-3-hydroxy-2-methyl-propionic acid and pyrrolidine.

Yield: 96% of theory, $C_{22}H_{27}N_3O_4$ (397.48)

Mass spectrum: $M^+$=398 $(M+Na)^+$=420 g. 2-[4-(N-benzyl-methylamino)-3-nitro-phenyl]-2-methyl-3-ethoxycarbonylmethyloxy-1-pyrrolidino-propan-1-one A solution of 8.0 g (20 mmol) of 2-[4-(N-benzyl-methylamino)-3-nitro-phenyl]-2-methyl-3-hydroxy-1-pyrrolidino-propan-1-one and 5 ml (48 mmol) of ethyl diazoacetate in 50 ml of methylene chloride is mixed with 2.0 ml of boron trifluoride-diethylether complex (16 mmol) at room temperature and refluxed for 14 hours. After cooling, the reaction solution is stirred into ice water and the organic phase is separated off. The aqueous phase is extracted three times with methylene chloride, the combined organic phases are washed with saline solution, dried over sodium sulphate and concentrated by evaporation. The residue is dissolved in ethyl acetate and purified on silica gel, extracting initially with petroleum ether, then with petroleum ether/ethyl acetate (1: 1). The uniform fractions are combined and concentrated by evaporation.

Yield: 2.5 g (26% of theory), $R_f$ value: 0.6 (silica gel; ethyl acetate)

$C_{26}H_{33}N_3O_6$ (483.57)

Mass spectrum: $(M+H)^+$=484 h. 2-(4-methylamino-3-amino-phenyl)-2-methyl-3-ethoxycarbonylmethyloxy-1-pyrrolidino-propan-1-one Prepared analogously to Example 1f from 2-[4-(N-benzyl-methylamino)-3-nitro-phenyl]-2-methyl-3-ethoxymethyloxy- 1-pyrrolidin- 1-yl-propan-1-one and hydrogen/palladium on activated charcoal.

Yield: 81% of theory, $R_f$ value: 0.40 (silica gel; methylene chloride/ethanol= 19:1)

i. 2-(4-cyanophenylaminomethyl)-1-methyl-5-[1-(ethoxycarbonylmethyloxmethyl)-1-(pyrrolidinocarbonyl)-ethyl-benzimidazole Prepared analogously to Example 1 g/h from 2-(4-methylamino-3 -amino-phenyl)-2-methyl-3-ethoxycarbonylmethyloxy-1-pyrrolidino-propan-1-one, 4-cyano-phenylglycine/O-(benzotriazol-1-yl)-N,N,N',N'-tetramethyluronium tetrafluoroborate and subsequently treated with glacial acetic acid.

Yield: 77% of theory, $R_f$ value: 0.40 (silica gel; methylene chloride/ethanol= 19:1)

$C_{28}H_{33}N_5O_4$ (503.61)

Mass spectrum: $(M+H)^+$=504 $(M+Na)^+$=526 k. 2-(4-amidinophenylaminomethyl)-1-methyl-5-[1-(ethoxycarbonylmethyloxymethyl)-1-(pyrrolidinocarbonyl)-ethyl]-benzimidazole-acetate Prepared analogously to Example 11 from 2-(4-cyanophenylaminomethyl)-1-methyl-5-[1-(ethoxycarbonylmethyloxymethyl)-1-(pyrrolidinocarbonyl)-ethyl]-benzimidazole and hydrochloric acid/ammonium carbonate in ethanol.

Yield: 64% of theory, $R_f$ value: 0.25 (silica gel; methylene chloride/ethanol= 4:1+1% glacial acetic acid)

$C_{28}H_{36}N_6O_4 \times CH_3COOH$ (520.63/580.69)

Mass spectrum: $(M+H)^+$=521

Example 6

2-(4-amidinophenylaminomethyl)-1-methyl-5-[1-(1H-tetrazol-5-yl-methyl)-1-(pyrrolidinocarbonyl)-ethyl]-benzimidazole-hydrochloride a. 2-[4-(N-benzyl-methylamino)-3-nitro-phenyl]-2-methyl-3-methanesulphonyloxy-1-prrolidino-propan-1-one A solution of 1.2 g (3.0 mmol) of 2-[4-(N-benzyl-methylamino)-3-nitro-phenyl]-2-methyl-3 -hydroxy-1-pyrrolidino-propan-1-one in 20 ml of tetrahydrofuran is combined at room temperature with 1.3 ml of (9.3 mmol) of triethylamine. Then 0.27 ml (3.5 mmol) of methanesulphonylchloride are added dropwise at 2–5° C. After 2 hours at room temperature the precipitate formed is suction filtered and the filtrate is concentrated by evaporation. The crude product is reacted further without purification.

Yield: 1.4 g (98% of theory).

b. 2-[4-(N-benzyl-methylamino)-3-nitro-phenyl]-2-methyl-3-cyano-1-pyrrolidine-propan-1-one A solution of 8.2 g (17 mmol) of 2-[4-(N-benzyl-methylamino)-3-nitro-phenyl]-2-methyl-3-methanesulphonyloxy-1-pyrrolidino-propan-1-one in 125 ml of dimethylformamide is mixed with 1.38 g (27 mmol) of potassium cyanide and heated to 100° C. for 2 hours. After cooling, the reaction solution is stirred into ice water and extracted 3× with ethyl acetate.

The combined organic phases are washed with saline solution and dried over sodium sulphate. The crude product is dissolved in methylene chloride and purified on silica gel, eluting initially with methylene chloride, then with methylene chloride/ethanol (50:1 and 25:1). The uniform fractions are combined and concentrated by evaporation.

Yield: 5.0 g (72% of theory)

$R_f$ value: 0.45 (silica gel; methylene chloride/ethanol= 19:1)

$C_{23}H_{26}N_4O_3$ (406.49)

Mass spectrum: $M^+$=406 $(M+Na)^+$=429 c. 2-[4-(N-benzyl-methylamino)-3-nitro-phenyl]-2-methyl-3-(1H-tetrazol-5-yl)-1-pyrrolidino-propan-1-one Prepared analogously to Example 4g from 2-[4-(N-benzyl-methylamino)-3-nitro-phenyl]-2-methyl-3-cyano-1-pyrrolidino-propan-1-one and tributyl tin azide.

Yield: 37% of theory, $R_f$ value: 0.55 (silica gel; methylene chloride/ethanol= 9:1)

$C_{23}H_{27}N_7O_3$ (449.52)

Mass spectrum: $(M+Na)^+$=472 $(M-H)^-$=448 d. 2-[4-(N-methylamino)-3-amino-phenyl]-2-methyl-3-(1H-tetrazol-5-yl)-1-pyrrolidino-propan-1-one Prepared analogously to Example 1f from 2-[4-(N-benzyl-methylamino)-3-nitro-phenyl]-2-methyl-3-(1H-tetrazol-5-yl)-1-pyrrolidino-propan-1-one and hydrogen/palladium on activated charcoal.

Yield: 48% of theory, $R_f$ value: 0.3 (silica gel; methylene chloride/ethanol=9:1)

$C_{16}H_{23}N_7O$ (329.41)

Mass spectrum: $(M+H)^+$=330 $(M-H)^-$=328 e. 2-(4-cyanophenylaminomethyl)-1-methyl-5-[1-(1H-tetrazol-5-yl-methyl)-1-(pyrrolidinocarbonyl)-ethyl]-benzimidazole Prepared analogously to Example 1g/h from 2-[4-(N-methylamino)-3-amino-phenyl]-2-methyl-3-(1H-tetrazol-5-yl)-1-pyrrolidino-propan-1-one, 4-cyano-phenylglycine/O-(benzotriazol-1-yl)-N,N,N',N'-tetramethyluronium tetrafluoroborate and subsequently treating with glacial acetic acid.

Yield: 17% of theory, $R_f$ value: 0.25 (silica gel; methylene chloride/ethanol= 9:1)

$C_{25}H_{27}N_9O$ (469.55)

Mass spectrum: $(M-H)^-$=468 f. 2-(4-amidinophenylaminomethyl)-1-methyl-5-[1-(1H-tetrazol-5-yl-methyl-D-1-(pyrrolidinocarbonyl)-ethyl]-benzimidazole-hydrochloride Prepared analogously to Example 11 from 2-(4-cyanophenylaminomethyl)-1-methyl-5-[1-(1H-tetrazol-5-yl-methyl)-1-(pyrrolidinocarbonyl)-ethyl]-benzimidazole and hydrochloric acid/ammonium carbonate in ethanol.

Yield: 25% of theory, $R_f$ value: 0.35 (Reversed phase RP8; 5% saline solution/methanol=1:1)

$C_{25}H_{30}N_{10}O \times HCl$ (486.58/523.05)

Mass spectrum: $(M+H)^+$=487

Example 7

2-(4-amidinophenylaminomethyl)-1-methyl-5-1-(ethoxycarbonylmethylaminomethyl)-1-(pyrrolidinocarbonyl)-ethyl]-benzimidazole-diacetate a. 2-[4-(N-benzyl-methylamino)-3-nitro-phenyl]-2-methyl-3-azido-1-pyrrolidino-propan-1-one Prepared analogously to Example 6b from 2-[4-(N-benzyl-methylamino)-3-nitro-phenyl]-2-methyl-3-methanesulphonyloxy-1-pyrrolidino-propan-1-one and sodium azide in dimethylformamide.

Yield: 100% of theory, $R_f$ value: 0.75 (silica gel; ethyl acetate/petroleum ether= 1:1)

$C_{22}H_{26}N_6O_3$ (422.49)

Mass spectrum: $M^+$=422 b. 2-[4-(N-benzyl-methylamino)-3-nitro-phenyl]-2-methyl-3-amino-1-pyrrolidino-propan-1-one A solution of 24.75 g (59 mmol) of 2-[4-(N-benzyl-methylamino)-3-nitro-phenyl]-2-methyl-3-azido-1-pyrrolidino-propan-1-one and 15.7 g (60 mmol) of triphenylphosphine in 250 ml of tetrahydrofuran and 1.8 ml of water is stirred for 60 hours at room temperature. After evaporation of the solvent the residue is purified over silica gel, eluting first with methylene chloride, then with methylene chloride/ethanol (50:1, 9:1, 8:2 and 7:3). The uniform fractions are combined and concentrated by evaporation.

Yield: 21.7 g (93% of theory), $R_f$ value: 0.25 (Reversed phase RP8; 5% saline solution/methanol=2:3)

$C_{22}H_{28}N_4O_3$ (396.49)

Mass spectrum: $(M+H)^+$=397 c. 2-[4-(N-benzyl-methylamino)-3-nitro-phenyl]-2-methyl-3-tert.butyloxycarbonylamino-1-pyrrolidino-propan-1-one Prepared analogously to Example 1c from 2-[4-(N-benzyl-methylamino)-3-nitro-phenyl]-2-methyl-3-amino-1-pyrrolidino-propan-1-one and di-tert.butyldicarbonate/N-ethyl-diisopropylamine in dioxane.

Yield: 98% of theory, $R_f$ value: 0.55 (silica gel; methylene chloride/ethanol= 19:1)

$C_{27}H_{36}N_5O_4$ (496.61)

Mass spectrum: $M^+$=496 $(M+Na)^+$=519 $(M-H)^-$=495 d. 2-[4-(N-methylamino)-3-amino-phenyl]-2-methyl-3-tert.butyloxycarbonylamino-1-pyrrolidino-propan-1-one Prepared analogously to Example 1f from 2-[4-(N-benzyl-methylamino)-3-nitro-phenyl]-2-methyl-3 -tert.butyloxycarbonylamino-1-pyrrolidino-propan-1-one and hydrogen/palladium on activated charcoal.

Yield: 23% of theory, $R_f$ value: 0.4 (silica gel; methylene chloride/ethanol=19:1)

$C_{20}H_{32}N_4O_3$ (376.5)

Mass spectrum: $(M+Na)^+=399$ $(M-H)^-=375$ e. 2-(4-cyanophenylaminomethyl)-1-methyl-5-[1-(tert.butyloxycarbonylaminomethyl)-1-(pyrrolidinocarbonyl)-ethyl]-benzimidazole Prepared analogously to Example 1g/h from 2-[4-(N-methylamino)-3-amino-phenyl]-2-methyl-3-(tert.butyloxycarbonylamino)-1-pyrrolidino-propan-1-one, 4-cyano-phenylglycine/carbonyldiimidazole and subsequent treatment with glacial acetic acid.

Yield: 58% of theory, $R_f$ value: 0.5 (aluminium oxide; methylene chloride/ethanol=19:1)

$C_{29}H_{36}N_6O_3$ (516.65)

Mass spectrum: $M^+=516$ $(M+Na)^+=539$ f. 2-(4-cyanophenylaminomethyl)-1-methyl-5-[1-aminomethyl-1-(pyrrolidinocarbonyl)-ethyl]-benzimidazole Prepared analogously to Example 1i from 2-(4-cyanophenylaminomethyl)-1-methyl-5-[1-(tert.butyloxycarbonylaminomethyl)-1-(pyrrolidinocarbonyl)-ethyl]-benzimidazole and 6N hydrochloric acid in dioxane.

Yield: 82% of theory, $R_f$ value: 0.25 (silica gel; methylene chloride/ethanol 9:1)

g. 2-(4-cyanophenylaminomethyl)-1-methyl-5-[1-(ethoxycarbonylmethylaminomethyl)-1-(pyrrolidinocarbonyl)-ethyl]-benzimidazole Prepared analogously to Example 1k from 2-(4-cyanophenylamino-methyl)-1-methyl-5-[1-aminomethyl-1-(pyrrolidinocarbonyl)-ethyl]-benzimidazole and ethyl bromoacetate/potassium carbonate in acetone.

Yield: 25% of theory, $R_f$ value: 0.6 (silica gel; methylene chloride/ethanol=9:1)

$C_{28}H_{34}N_6O_3$ (502.62)

Mass spectrum: $(M+H)^+=503$ $(M+Na)^+=525$ $(M-H)^-=501$ h. 2-(4-amidinophenylaminomethyl)-1-methyl-5-[1-(ethoxycarbonylmethylaminomethyl)-1-(pyrrolidinocarbonyl)-ethyl]-benzimidazole-diacetate Prepared analogously to Example 11 from 2-(4-cyanophenylaminomethyl)-1-methyl-5-[1-(ethoxycarbonylmethylaminomethyl)-1-(pyrrolidinocarbonyl)-ethyl]-benzimidazole and hydrochloric acid/ammonium carbonate in ethanol.

Yield: 66% of theory, $R_f$ value: 0.35 (silica gel; methylene chloride/ethanol=4:1+1% glacial acetic acid)

$C_{28}H_{37}N_7O_3 \times 2\ CH_3COOH$ (519.65/639.76)

Mass spectrum: $(M+H)^+=520$

The following compounds are obtained analogously to Example 7:

(1) 2-(4-amidinophenylaminomethyl)-1-methyl-5-[1-(N-(2-ethoxycarbonyl-ethyl)-N-methyl-aminomethyl)-1-(pyrrolidinocarbonyl)-ethyl]-benzimidazole (2) 2-(4-amidinophenylaminomethyl)-1-methyl-5-[1-(N-ethoxycarbonylmethylsulphonyl)-N-methyl-aminomethyl)-1-(pyrrolidinocarbonyl)-ethyl]-benzimidazole (3) 2-(4-amidinophenylaminomethyl)-1-methyl-5-[1-(N-ethoxycarbonylmethylaminocarbonyl-N-methyl-aminomethyl)-1-(2,5-dihydropyrrolocarbonyl)-ethyl]-benzimidazole-hydrochoride Yield: 55% of theory, $R_f$ value: 0.4 (Reversed phase RP8; 5% saline solution/methanol=1:1)

$C_{30}H_{38}N_8O_4 \times HCl$ (574.36/610.81)

Mass spectrum: $(M+H)^+=575$ $(M-H)^-=573$ $(M+Cl)^-=609/611$ (Cl)

Example 8

(R)-2-(4-amidinophenylaminomethyl)-1-methyl-5-[1-(carboxymethylamino)-1-[(R,S)-2-methyl-pyrrolidinocarbonyl]-ethyl]-benzimidazole-dihydrochloride (mixture of diastereomers)

A solution of 500 mg (0.84 mmol) of (R)-2-(4-amidinophenylaminomethyl)-1-methyl-5-[1-(ethoxycarbonylmethylamino)-1-[(R,S)-2-methyl-pyrrolidinocarbonyl]-ethyl]-benzimidazole-dihydrochloride (mixture of diastereomers) in 4 ml of water is mixed with 2.7 ml of 1N sodium hydroxide solution and stirred for 45 minutes at room temperature. The pH value of the solution is adjusted to 3.5 by adding 1N hydrochloric acid. The solution is concentrated by evaporation with the addition of toluene and the residue is mixed with a little methanol. After the undissolved inorganic material has been filtered off, the filtrate is concentrated by evaporation and triturated with ether. The solid formed is filtered off and dried.

Yield: 480 mg (100% of theory), $R_f$ value: 0.5 (Reversed phase RP8; 5% saline solution/methanol=1:1)

$C_{26}H_{33}N_7O_3 \times 2\ HCl$ (491.6/564.51)

Mass spectrum: $(M+H)^+=492$ $(M+Na)^+=514$

The following compounds are obtained analogously to Example 8:

(1) 2-(4-amidinophenylaminomethyl)-1-methyl-5-[1-(carboxymethylaminomethyl)-1-(pyrrolidinocarbonyl)-ethyl]-benzimidazole-dihydrochloride Yield: 70% of theory, $R_f$ value: 0.45 (Reversed phase RP8; 5% saline solution/methanol=1:1)

$C_{26}H_{33}N_7O_3 \times 2\ HCl$ (491.6/564.51)

Mass spectrum: $(M+H)^+=492$ (2) 2-(4-amidinophenylaminomethyl)-1-methyl-5-[1-(carboxymethylamino)-1-(2,5-dihydropyrrolocarbonyl)-ethyl]-benzimidazole-dihydrochloride Yield: 100% of theory, $R_f$ value: 0.5 (Reversed phase RP8; 5% saline solution/methanol=1:1)

$C_{25}H_{29}N_7O_3 \times 2\ HCl$ (475.55/548.46)

Mass spectrum: $(M+H)^+=476$ $(M-H)^-=474$ (3) (R)-2-[4-(N-phenylcarbonylamidino)-phenylaminomethyl]-1-methyl-5-[1-(carboxymethylamino)-1-(pyrrolidinocarbonyl)-ethyl]-benzimidazole Yield: 67% of theory, $R_f$ value: 0.46 (silica gel; 5% methylene chloride/methanol/conc. ammonia=4:0.9:0.1)

$C_{32}H_{35}N_7O_4$ (581.67)

Mass spectrum: $(M+H)^+=582$ $(M-H)^-=580$ $(M+Na)^+=604$ (4) 2-(4-amidinophenylaminomethyl)-1-methyl-5-[1-(carboxymethyloxymethyl)-1-(pyrrolidinocarbonyl)-ethyl]-benzimidazole-hydrochloride Yield: 45% of theory, $R_f$ value: 0.4 (Reversed phase RP8; 5% saline solution/methanol=1:1)

$C_{26}H_{32}N_6O_4 \times HCl$ (492.58/529.03)

Mass spectrum: $(M+H)^+=493$ $(M-H)^-=491$ (5) 2-(4-amidinophenylaminomethyl)-1-methyl-5-[1-(N-(2-carboxyethyl)-N-methyl-aminomethyl)-1-(pyrrolidinocarbonyl)-ethyl]-benzimidazole (6) 2-(4-amidinophenylaminomethyl)-1-methyl-5-[1-(N-carboxymethylsulphonyl-N-methyl-aminomethyl)-1-(pyrrolidinocarbonyl)-ethyl]-benzimidazole (7) 2-(4-amidinophenylaminomethyl)-1-methyl-5-[1-(N-carboxymethyaminocarbonyl)-N-methyl-aminomethyl)-1-(2,5-dihydropyrrolocarbonyl)-ethyl]-benzimidazole-hydrochloride Yield: 15% of theory, $R_f$ value: 0.5 (Reversed phase RP8; 5% saline solution/methanol=1:1)

$C_{28}H_{34}N_8O_4 \times HCl$ (546.62/583.09)

Mass spectrum: $(M+H)^+=547$ $(M-H)^-=545$ $(M+Cl)^-=581/583$ (Cl)

Example 9

Dry ampoule containing 75 mg of active substance per 10 ml

| Composition: | |
|---|---|
| Active substance | 75.0 mg |
| Mannitol | 50.0 mg |
| water for injections | ad 10.0 ml |

Preparation:

Active substance and mannitol are dissolved in water. After packaging the solution is freeze-dried. To produce the solution ready for use, the product is dissolved in water for injections.

Example 10

Dry ampoule containing 35 mg of active substance per 2 ml

| Composition: | |
|---|---|
| Active substance | 35.0 mg |
| Mannitol | 100.0 mg |
| water for injections | ad 2.0 ml |

Preparation:

Active substance and mannitol are dissolved in water. After packaging, the solution is freeze-dried.

To produce the solution ready for use, the product is dissolved in water for injections.

Example 11

Tablet containing 50 mg of active substance

| Composition: | |
|---|---|
| (1) Active substance | 50.0 mg |
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side.

Diameter of the tablets: 9 mm.

Example 12

Tablet containing 350 mg of active substance

| Preparation: | |
|---|---|
| (1) Active substance | 350.0 mg |
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

(1), (2) and (3) are mixed together and granulated with an aqueous solution of (4). (5) is added to the dried granulated material. From this mixture tablets are pressed, biplanar, faceted on both sides and with a dividing notch on one side.

Diameter of the tablets: 12 mm.

Example 13

Capsules containing 50 mg of active substance

| Composition: | |
|---|---|
| (1) Active substance | 50.0 mg |
| (2) Dried maize starch | 58.0 mg |
| (3) Powdered lactose | 50.0 mg |
| (4) Magnesium stearate | 2.0 mg |
| | 160.0 mg |

Preparation:

(1) is triturated with (3). This trituration is added to the mixture of (2) and (4) with vigorous mixing.

This powder mixture is packed into size 3 hard gelatin capsules in a capsule filling machine.

Example 14

Capsules containing 350 mg of active substance

| Composition: | |
|---|---|
| (1) Active substance | 350.0 mg |
| (2) Dried maize starch | 46.0 mg |
| (3) Powdered lactose | 30.0 mg |
| (4) Magnesium stear | 4.0 mg |
| | 430.0 mg |

Preparation:

(1) is triturated with (3). This trituration is added to the mixture of (2) and (4) with vigorous mixing.

This powder mixture is packed into size 0 hard gelatin capsules in a capsule filling machine.

Example 15

Suppositories containing 100 mg of active substance 1 suppository contains:

| | |
|---|---|
| Active substance | 100.0 mg |
| Polyethyleneglycol (M.W. 1500) | 600.0 mg |
| Polyethyleneglycol (M.W. 6000) | 460.0 mg |
| Polyethylenesorbitan monostearate | 840.0 mg |
| | 2,000.0 mg |

Method:

The polyethyleneglycol is melted together with polyethylene sorbitan monostearate. At 40° C. the ground active substance is homogeneously dispersed in the melt. It is cooled to 38° C. and poured into slightly chilled suppository moulds.

What is claimed is:
1. A compound selected from the group consisting of:
   (a) 2-(4-amidinophenylaminomethyl)-1-methyl-5-[1-(ethoxycarbonylmethylamino)-1-(2,5-dihydropyrrolocarbonyl)-ethyl]-benzimidazole,
   (b) 2-[4-(N-phenylcarbonylamidino)-phenylaminomethyl]-1-methyl-5-[1-(ethoxycarbonylmethylamino)-1-(2,5-dihydropyrrolocarbonyl)-ethyl]-benzimidazole,
   (c) (R)-2-[4-(N-phenylcarbonylamidino)-phenylaminomethyl]-1-methyl-5-[1-(isobutyloxycarbonylmethylamino)-1-(pyrrolidinocarbonyl)-ethyl]-benzimidazole,
   (d) (R)-2-[4-(N-phenylcarbonylamidino)-phenylaminomethyl]-1-methyl-5-[1-(n-propyloxycarbonylmethylamino)-1-(pyrrolidinocarbonyl)-ethyl]-benzimidazole,
   (e) (R)-2-(4-amidinophenylaminomethyl)-1-methyl-5-[1-(carboxymethylamino)-1-[(R,S)-2-methyl-pyrrolidinocarbonyl]-ethyl]-benzimidazole,
   (f) 2-(4-amidinophenylaminomethyl)-1-methyl-5-[1-(carboxymethylamino)-1-(2,5-dihydropyrrolocarbonyl)-ethyl]-benzimidazole and
   (g) (R)-2-[4-(N-phenylcarbonylamidino)-phenylaminomethyl]-1-methyl-5-[1-(cyclohexyloxycarbonylmethylamino)-1-(2,5-dihydropyrrolocarbonyl)-ethyl]-benzimidazole,
   or a tautomer or physiologically acceptable salt thereof.
2. (R)-2-[4-(N-phenylcarbonylamidino)-phenylaminomethyl]-1-methyl-5-[1-(n-propyloxycarbonylmethylamino)-1-(pyrrolidinocarbonyl)-ethyl]-benzimidazole.
3. A pharmaceutical composition containing a compound according to claim 1 or 2, and a pharmaceutically acceptable carrier.
4. A method for inhibiting the formation of thromboses or for treating thromboses which method comprises administering to a host in need of such treatment an antithrombotic amount of a compound according to claim 1 or 2.

* * * * *